United States Patent [19]

Kawamura et al.

[11] Patent Number: 5,358,788
[45] Date of Patent: Oct. 25, 1994

[54] ORGANIC ELECTROLUMINESCENCE DEVICE CONTAINING A SILANAMINE COMPOUND

[75] Inventors: Hisayuki Kawamura; Chishio Hosokawa; Tadashi Kusumoto, all of Sodegaura, Japan

[73] Assignee: Idemitsu Kosan Company Limited, Tokyo, Japan

[21] Appl. No.: 35,676

[22] Filed: Mar. 23, 1993

[30] Foreign Application Priority Data

Apr. 2, 1992 [JP] Japan .................................. 4-080980

[51] Int. Cl.$^5$ .............................................. B32B 9/00
[52] U.S. Cl. ................................. 428/446; 313/504;
428/411.1; 428/448; 428/450; 428/457;
428/690; 428/704; 428/917
[58] Field of Search ............... 556/410; 428/917, 690,
428/446, 448, 411.1, 450, 457, 704; 313/504;
430/58, 59; 252/301.16

[56] References Cited

U.S. PATENT DOCUMENTS 4,720,432  1/1988  VanSlyke et al. .................... 428/457
4,950,950  8/1990  Perry et al. .......................... 313/504

FOREIGN PATENT DOCUMENTS 0446895  9/1991  European Pat. Off. .
63-295695  12/1988  Japan .

OTHER PUBLICATIONS

Atilla Nagy et al, "HeI and HeII photoelectron spectroscopic investigation of substituent effects in aminosilanes", Journal of Organometallic Chemistry, vol. 419, No. -2, 1991, pp. 27–42.

*Primary Examiner*—Patrick J. Ryan
*Assistant Examiner*—Marie R. Macholl
*Attorney, Agent, or Firm*—Frishauf, Holtz, Goodman & Woodward

[57] ABSTRACT

An electroluminescence device which includes an organic light-emitting layer and optionally one or more further layers disposed between a pair of electrodes, wherein at least one of the layers contains a silanamine compound which has the formula (I),

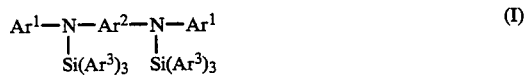

wherein each of $Ar^1$ and $Ar^3$ is an optionally substituted aryl group and $Ar^2$ is an optionally substituted arylene group.

16 Claims, 1 Drawing Sheet

ORGANIC ELECTROLUMINESCENCE DEVICE CONTAINING A SILANAMINE COMPOUND

BACKGROUND OF THE INVENTION

1. Field of the Invention

The present invention relates to a silanamine derivative, particularly a silanamine derivative usable as a material for an organic electroluminescence device and a photoconductive drum for electrophotography, and a process for the production thereof. The present invention also relates to an organic electroluminescence device using the above silanamine derivative.

2. Description of Prior Art

Silanamine derivatives typified by N,N'-ditrimethylsilyluric acid, N-trimethylsilylimidazole and trimethylsilyldiethylamine are compounds having Si-N bonds, and these compounds are conventionally used as silylating reagents.

U.S. Pat. No. 4,950,950 discloses cyclodisilazanes usable as materials for forming a hole-conducting layer constituting an organic electroluminescence device (to be referred to as "EL device" hereinafter).

Meanwhile, as other compounds preferred as materials for forming a hole-conducting layer, there are known aromatic tertiary amines (including monoamines, diamines and triamines, to be sometimes referred to as "amino compounds", see JP-A-63-295695 for example). The ionization potentials of the above amino compounds are generally lower than those of the above cyclodisilazanes. For example, TPD [N,N'-bis-(m-tolyl)-N,N'-diphenyl-1,1'-biphenyl], which is one of the diamino compounds, shows an ionization potential of about 5.5 eV, and hexaphenylcyclodisilazane, which is one of the cyclodisilazanes, shows an ionization potential of about 5.7 eV. Thus, the former shows a lower ionization potential than the latter.

When a hole-conducting layer has a low ionization potential, the actuation voltage of the organic EL device can be decreased. Therefore, the above amino compounds are much more preferred as a material for forming a hole-conducting layer than the above cyclodisilazanes.

Further, a charge-conducting material for forming an electrophotographic photoconductive drum is also required to have a low ionization potential.

However, the amino compounds have the following defects. That is, 4,4'-di-tert-butyl-triphenylamine is difficult to purify, and TPD, when formed into a thin film, undergoes recrystallization with time to deteriorate a service life of the device.

SUMMARY OF THE INVENTION

It is therefore a first object of the present invention to provide a silanamine derivative which is easy to purify, which undergoes deferred recrystallization with time when formed into a thin film, and which shows a low ionization potential, and a process for the production thereof.

Further, it is a second object of the present invention to provide a novel organic EL device which can be actuated at a low voltage.

According to the present invention, the above first object of the present invention is achieved by a silanamine derivative of the formula (I),

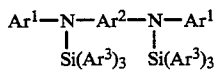

wherein:

each of $Ar^1$s is independently (i) an aryl group having 6 to 20 carbon atoms or (ii) an aryl group having 6 to 20 ring-forming carbon atoms and being substituted with an alkyl group having 1 to 6 carbon atoms, an alkoxy group having 1 to 6 carbon atoms, a phenoxy group, an alkyl-substituted phenoxy group or a vinyl group, $Ar^2$ is (i) an arylene group having 6 to 20 carbon atoms or (ii) an arylene group having 6 to 20 ring-forming carbon atoms and being substituted with an alkyl group having 1 to 6 carbon atoms, and each of $Ar^3$s is independently (i) an aryl group having 6 to 12 carbon atoms or (ii) an aryl group having 6 to 12 ring-forming carbon atoms and being substituted with an alkyl group having 1 to 3 carbon atoms.

The process for the production of the above silanamine derivative comprises reacting a diarylamine of the formula (II),

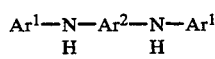

wherein:

each of $Ar^1$s is; independently (i) an aryl group having 6 to 20 carbon atoms or (ii) an aryl group having 6 to 20 ring-forming carbon atoms and being substituted with an alkyl group having 1 to 6 carbon atoms,an alkoxy group having 1 to 5 carbon atoms, a phenoxy group, an alkyl-substituted phenoxy group or a vinyl group, and $Ar^2$ is (i) an arylene group having 6 to 20 carbon atoms or (ii) an arylene group having 6 to 20 ring-forming carbon atoms and being substituted with an alkyl group having 1 to 6 carbon atoms, with a halogenated silane of the formula (III).

wherein $Ar^3$ is (i) an aryl group having 6 to 12 carbon atoms or (ii) an aryl group having 6 to 12 ring-forming carbon atoms and being substituted with an alkyl group having 1 to 3 carbon atoms, and X is a halogen atom.

According to the present invention, the above second object of the present invention is achieved by an organic EL device which comprises a single or plural compound layer(s) containing at least an organic light-emitting layer and a pair of electrodes sandwiching the compound layer(s), the compound layer(s) containing at least one layer containing the above silanamine derivative of the present invention.

DETAILED DESCRIPTION OF THE INVENTION

Figure 1:
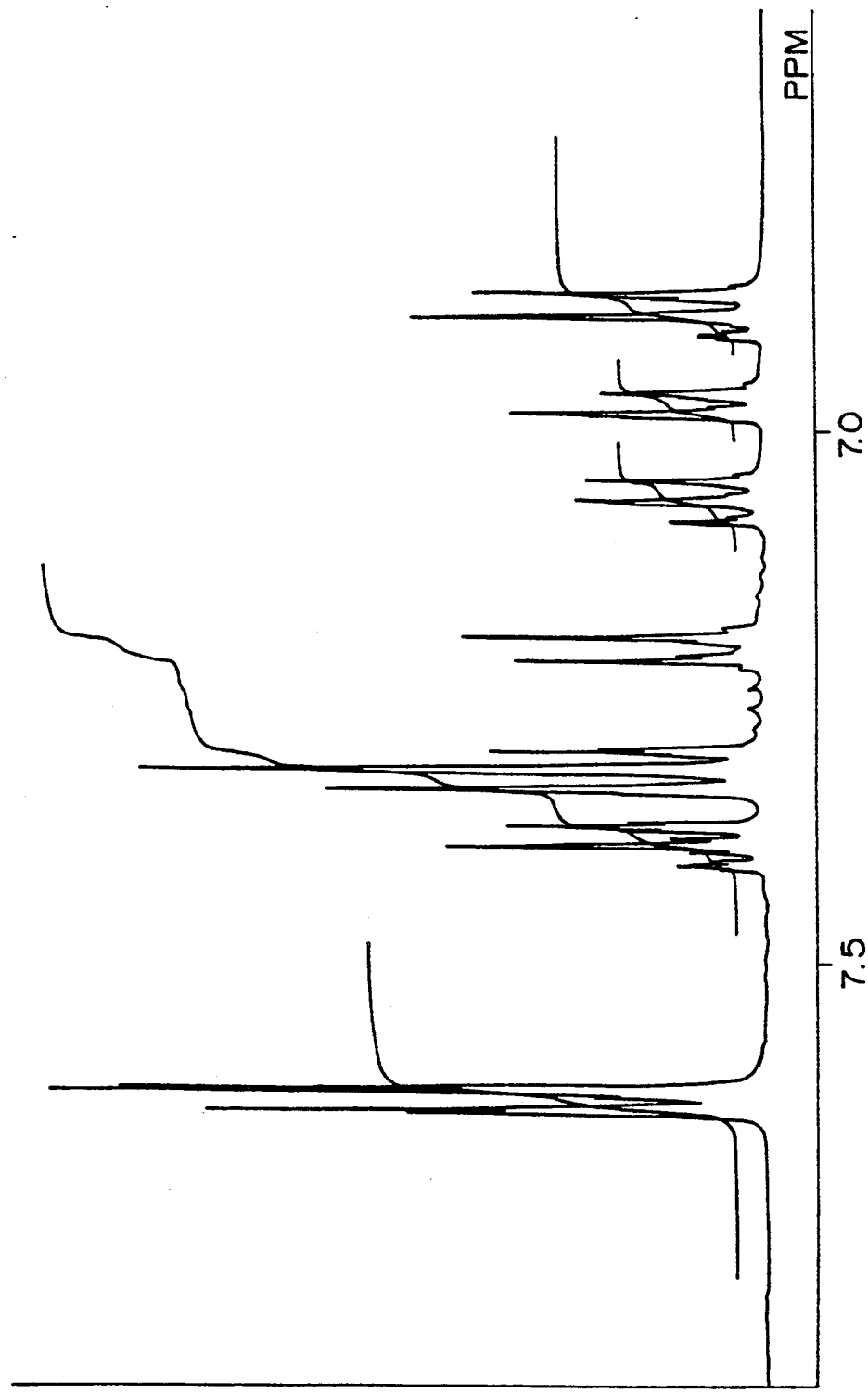
FIG. 1 is an NMR chart off a silanamine derivative obtained in Example 1.

The present invention will be described in detail below.

First, the silanamine derivative of the present invention will be explained. As described above, the silanamine derivative has the formula (I).

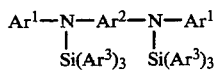

In the above formula (I), each of $Ar^1$s is independently (i) an aryl group having 6 to 20 carbon atoms or (ii) an aryl group having 6 to 20 ring-forming carbon atoms and being substituted with an alkyl group having 1 to 6 carbon atoms, an alkoxy group having 1 to 6 carbon atoms, a phenoxy group, an alkyl-substituted phenoxy group or a vinyl group.

Specific examples of the aryl group having 6 to 20 carbon atoms include phenyl, biphenyl, naphthyl, anthranyl, phenanthryl and pyrenyl. Specific examples of the alkyl group having 1 to 6 carbon atoms and being a substituent on the aryl group include methyl, ethyl, n-propyl, i-propyl, n-butyl, i-butyl, s-butyl, t-butyl, n-pentyl and n-hexyl. Specific examples of the alkoxy group having 1 to 6 carbon atoms and being a substituent on the aryl group include methoxy, ethoxy, propoxy, butoxy, pentoxy and hexoxy. Specific examples of the alkyl-substituted phenoxy group include a phenoxy group substituted with the above-described alkyl group having 1 to 6 carbon atoms.

In the above formula (I), $Ar^2$ is (i) an arylene group having 6 to 20 carbon atoms or (ii) an arylene group having 6 to 20 ring-forming carbon atoms and being substituted with an alkyl group having 1 to 6 carbon atoms.

Specific examples of the arylene group having 6 to 20 carbon atoms (arylene group having 6 to 20 ring-forming carbon atoms) include phenylene, biphenylene, naphthylene, anthranylene, phenanthrylene and pyrenylene. Specific examples of the alkyl group having 1 to 6 carbon acorns and being a substituent on the arylene group include those described regarding $Ar^1$.

In the above formula (I), each of $Ar^3$s is independently (i) an aryl group having 6 to 12 carbon atoms or (ii) an aryl group having 6 to 12 ring-forming carbon atoms and being substituted with an alkyl group having 1 to 3 carbon atoms.

Specific examples of the aryl group having 6 to 12 carbon atoms include phenyl, biphenyl, naphthyl, anthranyl, phenanthryl and pyrenyl. Specific examples of the alkyl group having 1 to 3 carbon atoms and being a substituent on the aryl group include methyl, ethyl, n-propyl and i-propyl.

Tables 1 to 8 show the specific examples of the silanamine derivative of the present invention.

TABLE 1

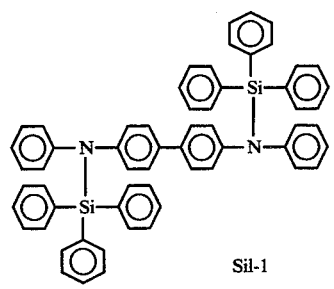

Sil-1

TABLE 1-continued

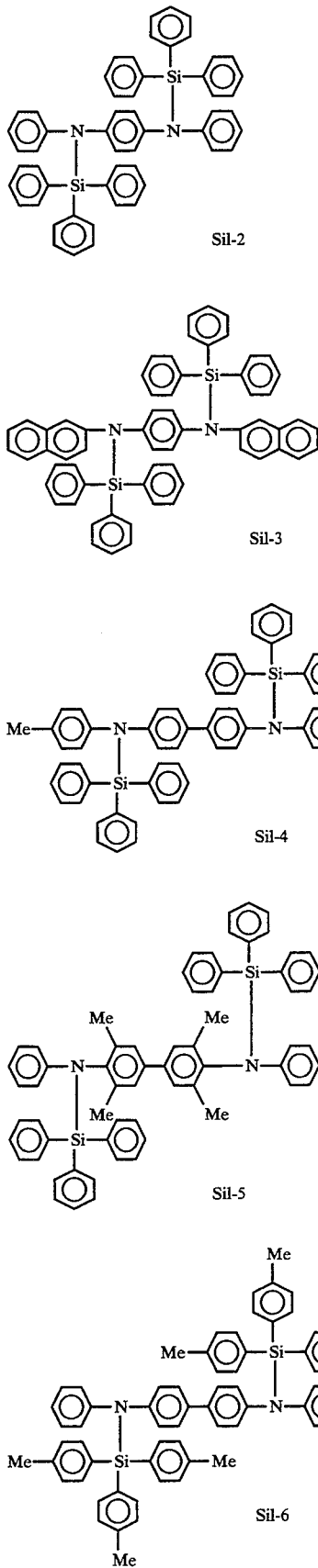

Sil-2

Sil-3

Sil-4

Sil-5

Sil-6

TABLE 2
(7)
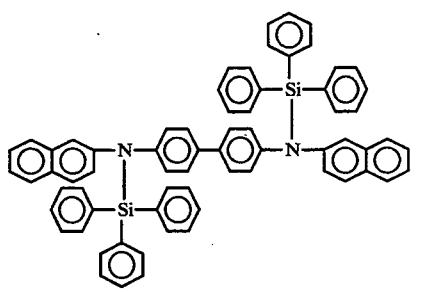
(8)
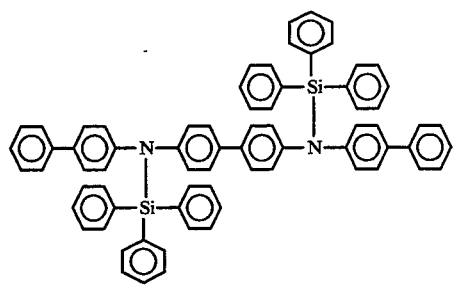
(9)
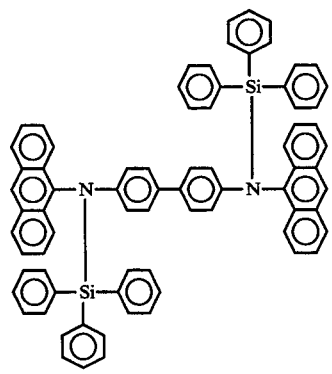
(10)
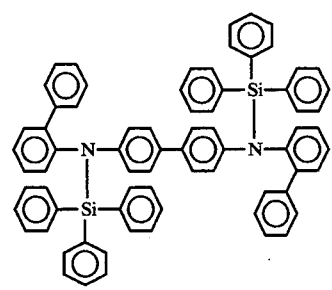
(11)
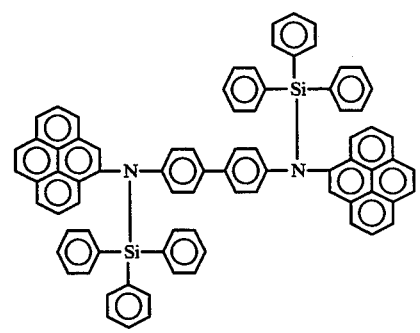
TABLE 2-continued
(12)
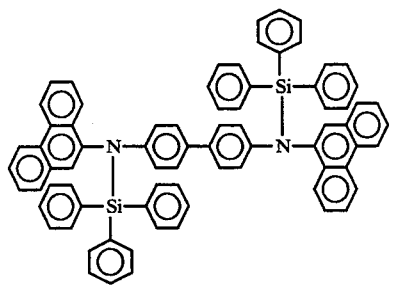
TABLE 3
(13)
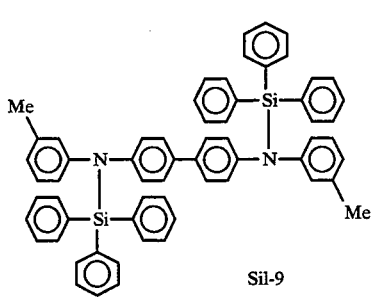
Sil-9
(14)
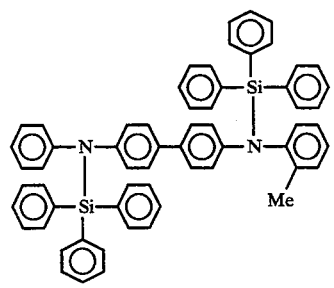
(15)
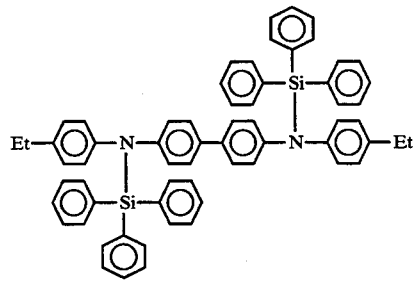
(16)
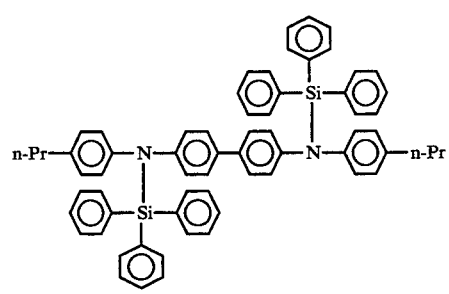

TABLE 3-continued
(17)
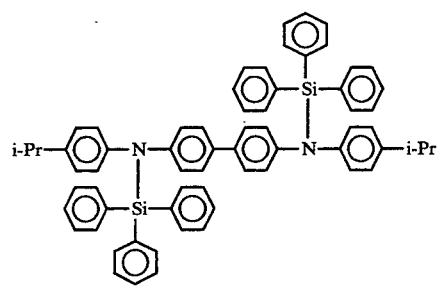
(18)
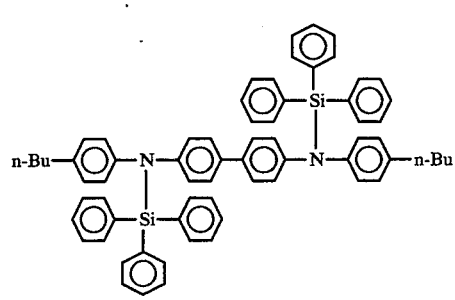
TABLE 4
(19)
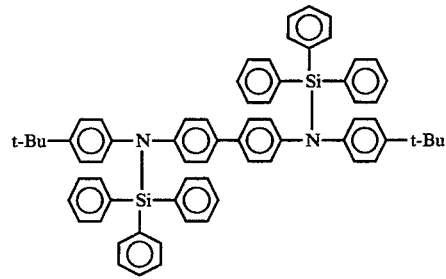
(20)
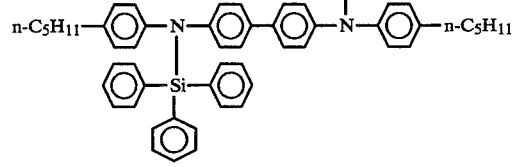
(21)
TABLE 4-continued
(22)
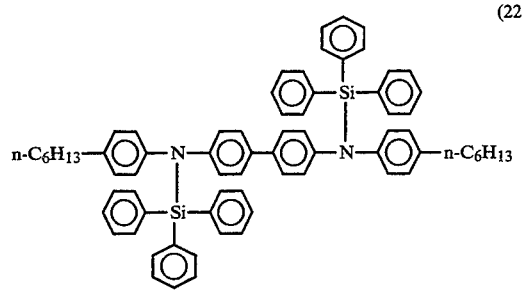
(23)
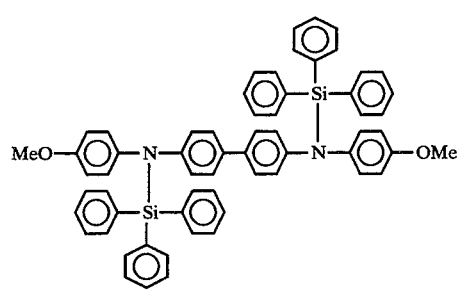
(24)
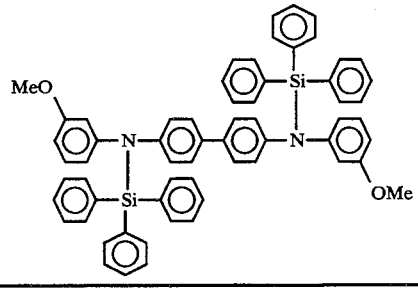
TABLE 5
(25)
(26)
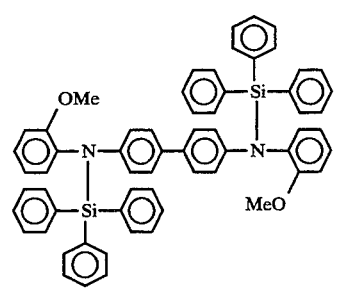

TABLE 5-continued
(27)
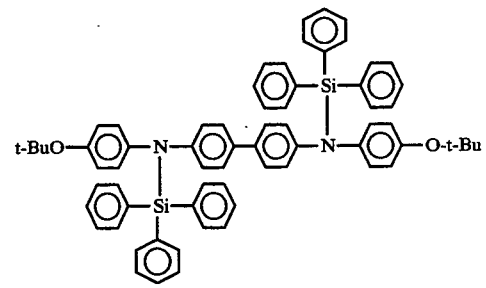
(28)
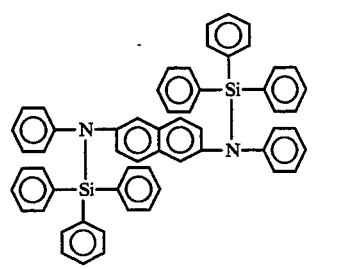
(29)
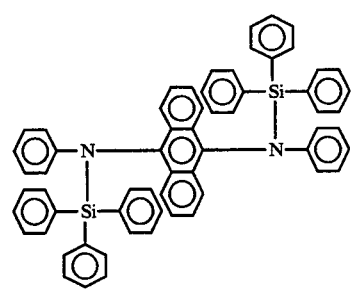
(30)
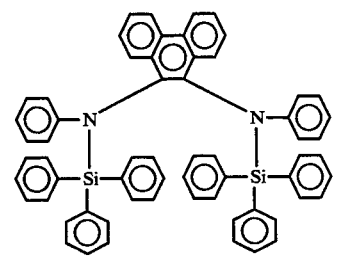
TABLE 6
(31)
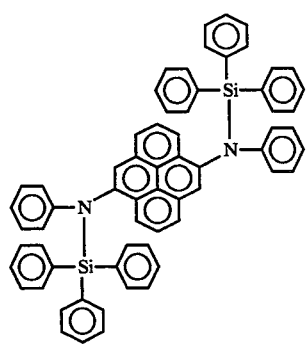
TABLE 6-continued
(32)
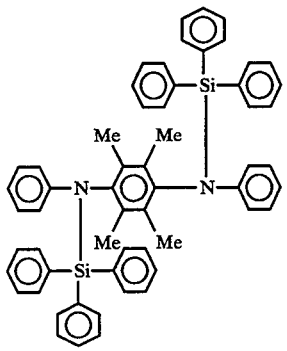
(33)
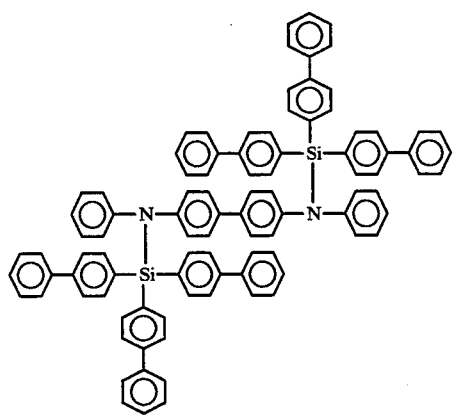
(34)
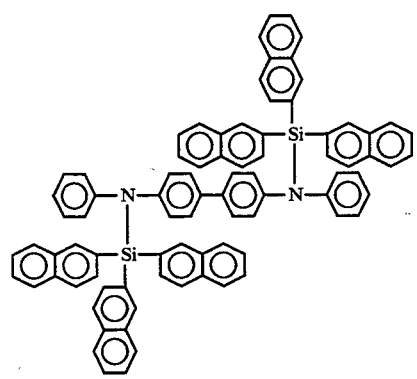
TABLE 7
(35)
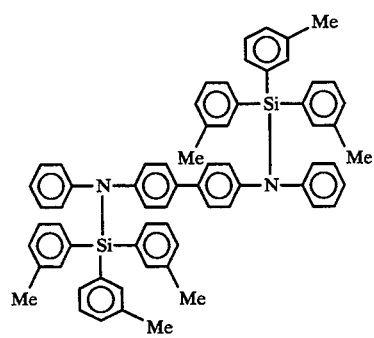

TABLE 7-continued

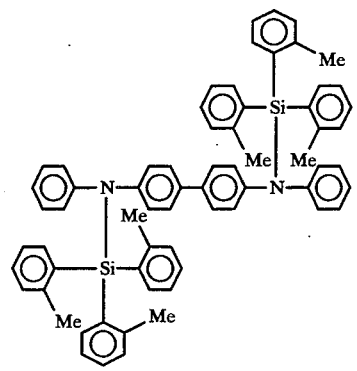
(36)

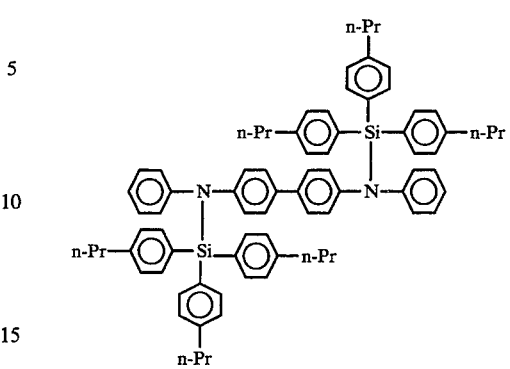
(38)

(37)

TABLE 8

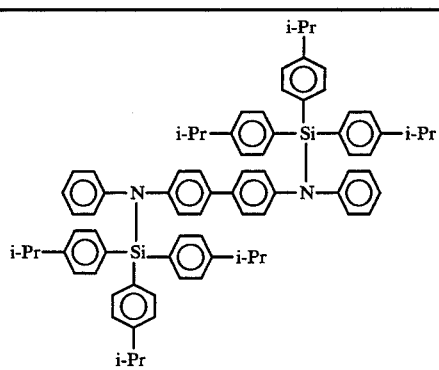
(39)

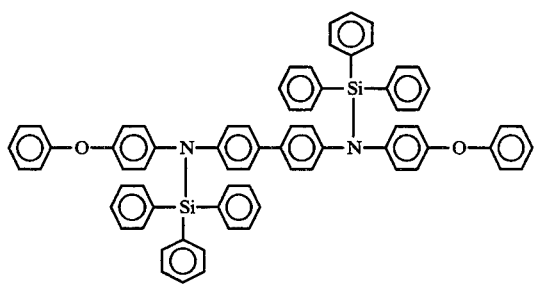
(40)

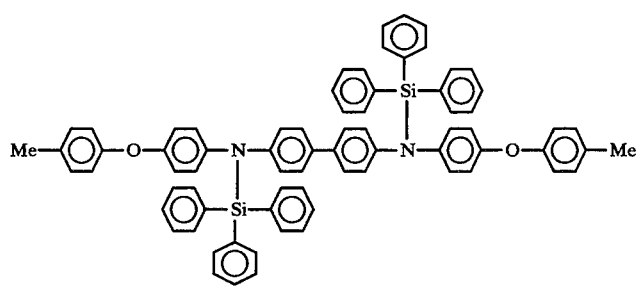
(41)

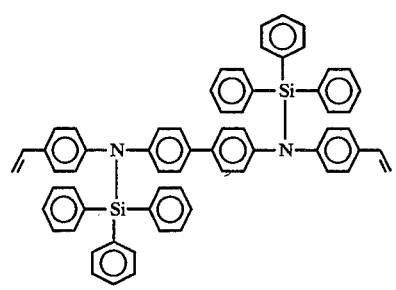
(42)

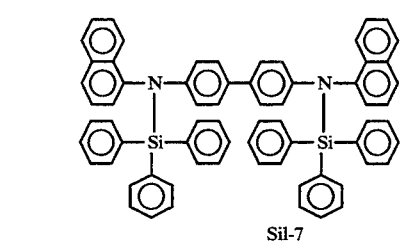
(44)
Sil-7

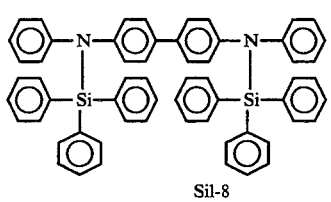
(44)
Sil-8

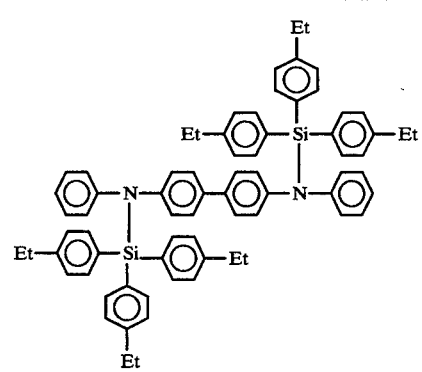

Differing from conventional silane derivatives, the silanamine derivative of the present invention has a characteristic feature in that its ionization potential is, for example, 5.6 eV or less.

The silanamine derivatives of the present invention can be easily formed into a thin film by a known vacuum vapor-deposition method. Further, it can be also easily formed into a thin film by any one of a casting method, a coating method and a spin coating method which use n dispersion of the silanamine derivative of the present invention in a polymer such as polycarbonate, polyurethane, polystyrene or polyester. The soformed thin film has an electronic function of hole transmission and has a characteristic feature that its recrystallization with time is deferred as compared with a thin film formed of a conventional amino compound (e.g., TPD).

The silanamine derivative of the present invention, having the above characteristic features, can be applied to a hole-conducting layer, a hole-conducting binder or a light-emitting layer of an organic EL device, and it can be also applied to a hole-conducting layer of an photoconductive drum for electrophotography. When applied to a organic EL device, the silanamine derivative of the present invention can decrease the voltage to be applied, since it has a low ionization potential of, e.g., 5.6 eV or lower. When applied to a photoconductive drum for electrophotography, the silanamine derivative of the present invention can achieve excellent injection of holes from a charge-generating layer. Further, it can be also used as an organic non-linear material, a luminescent material and a binder for firing ceramics.

The silanamine derivative of the present invention can be effectively synthesized, for example, by the following process of the present invention.

As described already, the process for the production of the above silanamine derivative, provided by the present invention, comprises reacting a diarylamine of the formula (II).

$$Ar^1-\underset{H}{N}-Ar^2-\underset{H}{N}-Ar^1 \quad (II)$$

with a halogenated silane of the formula (III), $$(Ar^3)_3SiX \quad (III).$$

$Ar^1$ and $Ar^2$ in the above formula (II) and $Ar^3$ in the above formula (III) are as defined in the formula (I) showing the silanamine derivative of the present invention. X in the formula (III) is a halogen atom, and specific examples of the halogen atom include fluorine, chlorine, bromine and iodine.

Tables 9 to 11 show specific examples of the diarylamine of the formula (II). Table 12 shows specific examples of the halogenated silane of the formula (III).

TABLE 9

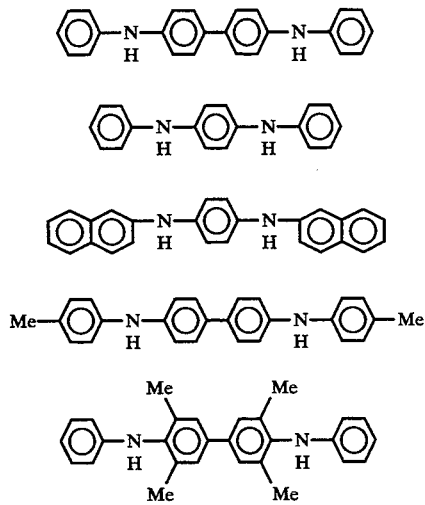

TABLE 9-continued

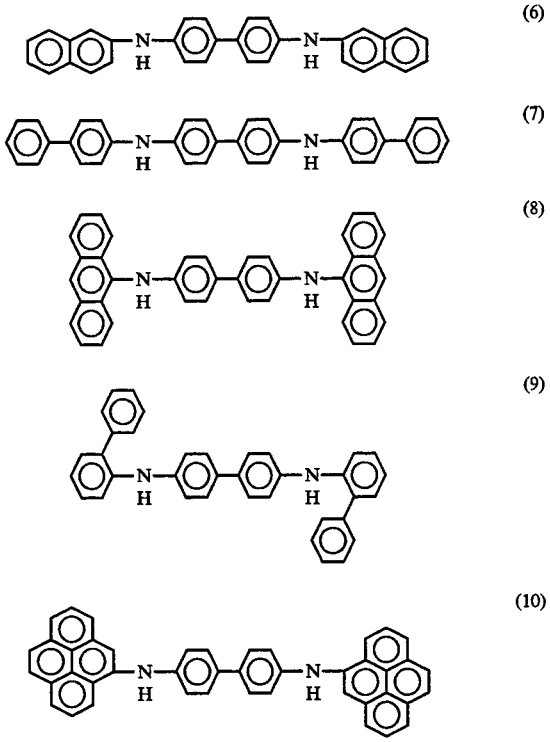

TABLE 10

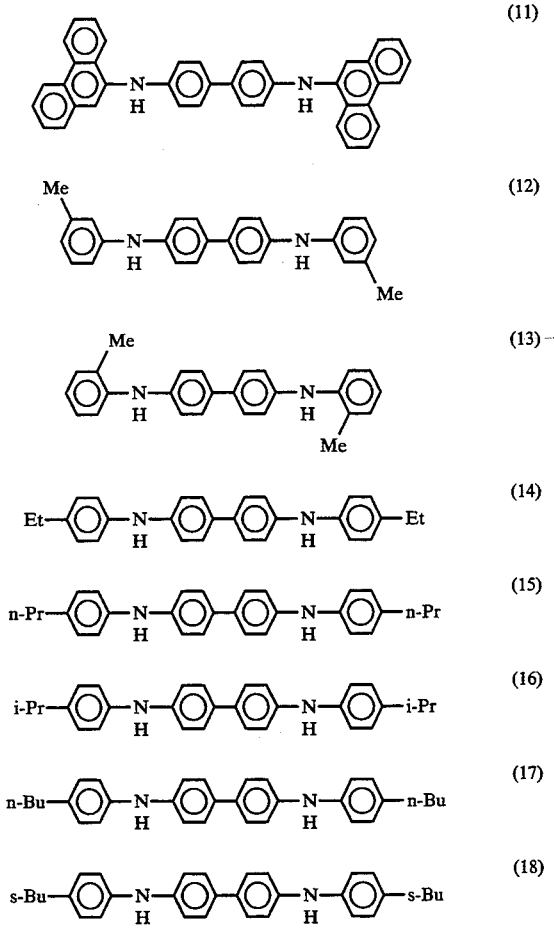

TABLE 10-continued
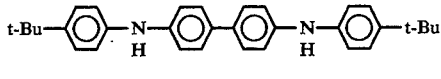 (19)
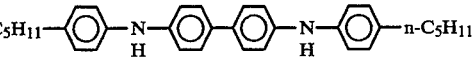 (20)
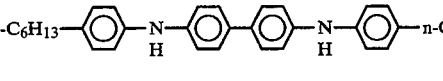 (21)
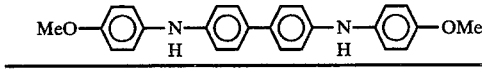 (22)
TABLE 11
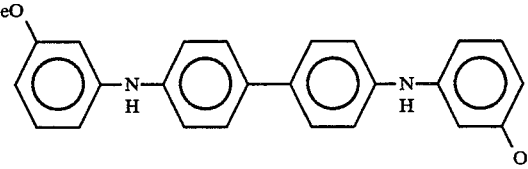 (23)
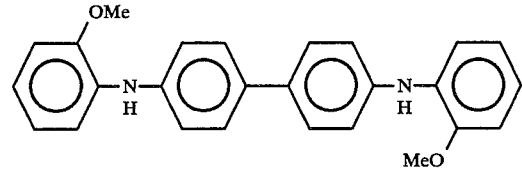 (24)
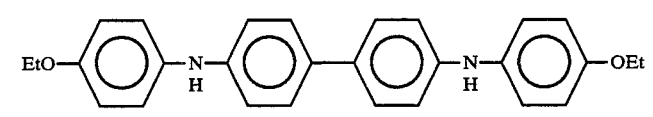 (25)
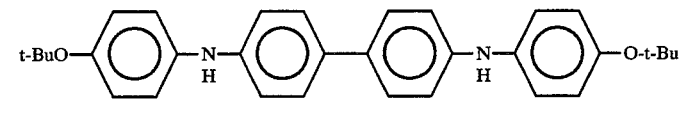 (26)
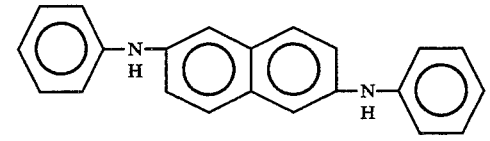 (27)
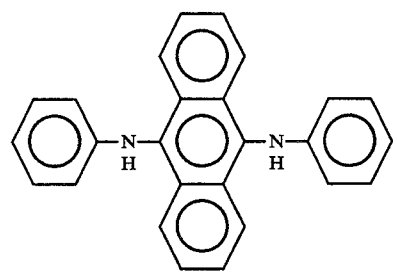 (28)
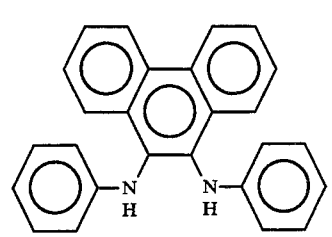 (29)

TABLE 11-continued
(30)
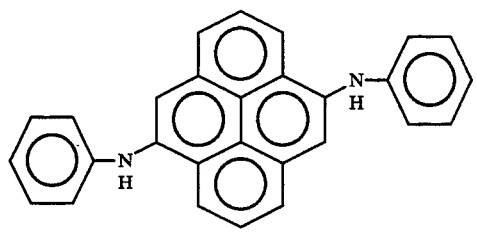
(31)
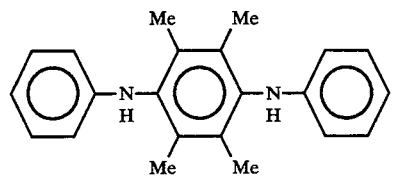
(32)
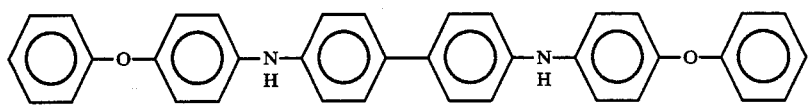
(33)
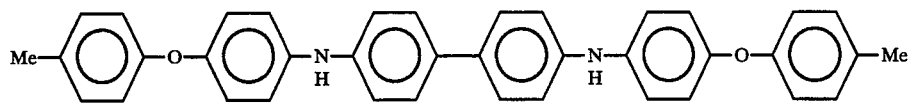
(34)
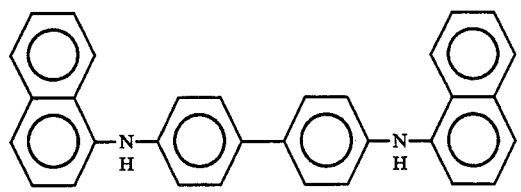
(35)
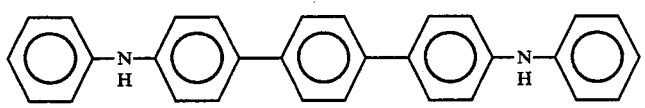
TABLE 12
(1)
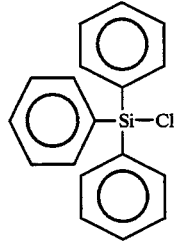
(2)
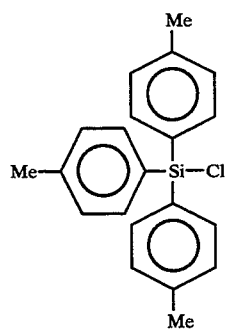
TABLE 12-continued
(3)
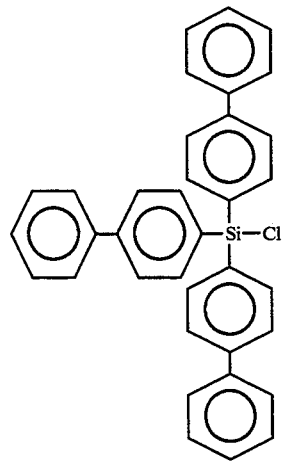

TABLE 12-continued (4) 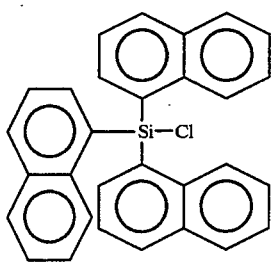

(5) 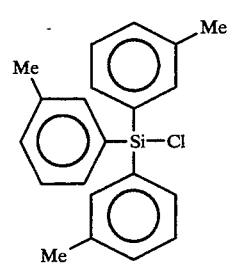

(6) 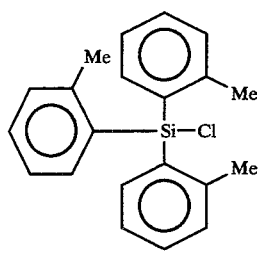

(7) 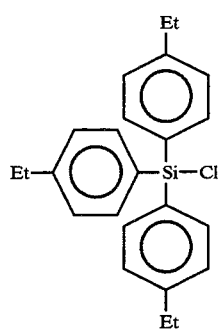

(8) 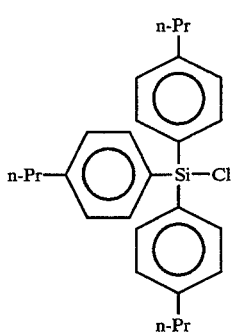

TABLE 12-continued (9) 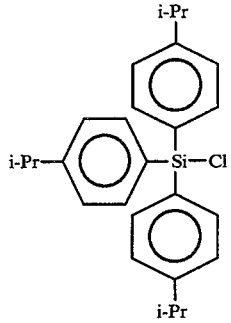

(10) 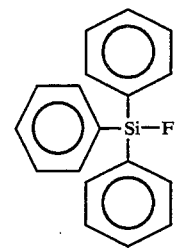

(11) 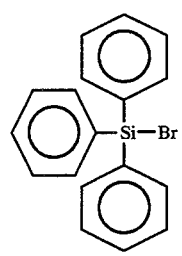

(12) 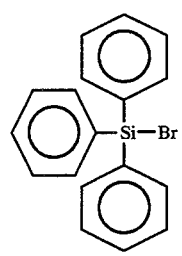

The diarylamine of the formula (II) and the halogenated silane of the formula (III) can be allowed to react, for example, by the following method.

At first, a reactor flushed with an inert gas such as an argon gas is charged with the diarylamine of the formula (II), and a solvent is added to dissolve the diarylamine. The solvent can be selected from diethyl ether, THF (tetrahydrofuran), dioxane, toluene and dimethoxyethane, preferred is THF, particularly THF obtained by distillation with a sodium wire under an argon atmosphere.

Then, 2 to 4 equivalent weights of a base is added to the above-prepared solution. The base is preferably selected from strong bases such as sodium alkoxide, sodium hydride, potassium t-butoxide, n-butyllithium and DBU (1,8-diazabicyclo[5.4.0.]undec-7-ene), particularly preferred is n-butyllithium. The amount of the base is preferably about 2.5 equivalent weights.

After the base is added, the resulting mixture is heated at approximately 30° to 120° C. for approximately 0.5 to 3 hours. It is desirable to heat the mixture for about 0.5 hours, and it is preferred to heat the mixture around 50° C.

Then, 2 to 4 equivalent weights of the halogenated silane of the formula (III) is dissolved in a solvent, and the resulting solution is added dropwise-to the above reaction mixture. This solvent can be selected from diethyl ether, THF, dioxane, toluene and dimethoxyethane, while it is preferred to use the same solvent as that used for dissolving the diarylamine. The amount of the halogenated silane is preferably about 2.5 equivalent weights. The reaction temperature can be properly set in the range of from $-78°$ C. to 120° C., while a sufficient result can be obtained even at room temperature. The reaction time can be properly set in the range of from 8 hours to 48 hours, while a sufficient result can be obtained when the reaction is carried out for about 18 hours.

The diarylamine of the formula (II) and the halogenated silane of the formula (III) are allowed to react as described above, whereby the silanamine derivative of the present invention can be produced.

The above-produced silanamine derivative of the present invention can be purified, for example, by the following method.

The reaction is terminated by adding water to the resulting mixture, and then the resulting mixture was subjected to extraction with a solvent. This solvent can be selected from toluene, dichloromethane and ethyl acetate. Dichloromethane is particularly preferred. After the extraction, the extract is dried, and the solvent is evaporated.

Then, the resultant residue is subjected to column chromatography to obtain the intended purified product. The solid support for the column chromatography can be selected from silica gel, alumina and the like. The developing solvent can be selected from toluene, dichloromethane and chloroform.

When the silanamine derivative is difficult to extract with a solvent, i.e., sparingly soluble in the solvent, it can be washed with hot pyridine to obtain the purified product.

The organic EL device of the present invention will be explained hereinafter. As described already, the organic EL device of the present invention comprises a single or plural compound layer(s) containing at least an organic light-emitting layer and a pair of electrodes sandwiching the compound layers(s), the compound layer(s) containing at least one layer containing the above silanamine derivative of the present invention.

The constitution of the organic EL device includes (1) anode/organic 1 light-emitting layer/cathode, (2) anode/hole-conducting layer/organic light-emitting layer/cathode, (3) anode/organic light-emitting layer/electron-injecting layer/cathode and [4) anode/-hole-conducting layer/organic light-emitting layer/electron-injecting layer/cathode. The organic EL device of the present invention may have any one of the above constitutions if at least one layer of the compound layer(s) sandwiched between a pair of electrodes (anode and cathode) contains the above silanamine derivative of the present invention (the compound layer(s) referring to an organic light-emitting layer in the device having the above constitution (1), a hole-conducting layer and an organic light-emitting layer in the device having the above constitution (2), an organic light-emitting layer and an electron-injecting layer in the device having the above constitution (3) and a hole-conducting layer, an organic light-emitting layer and an electron-injecting layer in the device having the above constitution (4)). The organic EL device having any one of the above constitutions is preferably supported on a substrate. This substrate is not specially limited, and can be selected from those substrates generally used for conventional organic EL devices, such as substrates formed of glass, a transparent plastic and quartz.

The layer containing the silanamine derivative, which is a characteristic part of the organic EL device of the present invention, is preferably a hole-conducting layer or an organic light-emitting layer, and it is particularly preferably a hole-conducting layer.

The hole-conducting layer containing the silanamine derivative may have the structure of a single layer formed of the silanamine derivative alone or a multi-layer formed of a layer element of the silanamine derivative and a layer element of a substance conventionally used as a material for a hole-conducting layer of an organic EL device. Further, it may have the structure of a single layer or multi-layer containing a mixture of the silanamine derivative and a substance conventionally used as a material for a hole-conducting layer of an organic EL device. The hole-conducting layer containing the silanamine derivative can be formed from the silanamine derivative and optionally other material for a hole-conducting layer by any one of a vapor-deposition method, a casting method, a coating method and a spin coating method. It can be also formed from a dispersion of the silanamine derivative in a transparent polymer such as polycarbonate, polyurethane, polystyrene, polyarylate, polyester, or the like by a casting method, a coating method or a spin coating method.

The organic light-emitting layer containing the silanamine derivative may have the structure of a single layer formed of the silanamine derivative alone or a multi-layer formed of a layer element of the silanamine derivative and a layer element of a substance conventionally used as a material for an organic light-emitting layer of an organic EL device. Further, it may have the structure of a single layer or multi-layer containing a mixture of the silanamine derivative and a substance conventionally used as a material for an organic light-emitting layer of an organic EL device. The organic light-emitting layer containing the silanamine derivative can be formed from the silanamine derivative and optionally other material for an organic right emitting layer by any one of a vapor-deposition method, a casting method, a coating method and a spin coating method.

In the organic EL device of the present invention, the layers other than the layer containing the silanamine derivative can be formed from the same materials as those used for conventional organic EL devices.

For example, the material for the anode can be preferably selected from metals having a large work function (at least 4 eV) and their alloys, electrically conductive compounds and mixtures of these. Specific examples thereof include metals such as Au and dielectric transparent materials such as CuI, ITO, $SnO_2$ and ZnO. The anode can be produced by forming a thin film of the above material by a vapor-deposition method or a sputtering method. When light emitted from the organic light-emitting layer is transmitted through the anode, the transmittance of the anode is preferably greater than 10%. The sheet resistance of the anode is preferably several hundreds $\Omega/\square$ or less. Although depending upon materials, the film thickness of the anode is generally 10 nm to 1 $\mu$m, preferably 10 to 200 nm.

The material for the cathode can be preferably selected from metals having a small work function (4 eV or less) and their alloys, electrically conductive compounds and mixtures of these. Specific examples thereof include sodium, sodium-potassium alloy, magnesium, lithium, a magnesium/copper mixture, Ai/Al$_2$O$_3$ and indium. The cathode can be produced by forming a thin film of the above material by a vapor-deposition method or a sputtering method. When light emitted from the organic light-emitting layer is transmitted through the cathode, the transmittance of the cathode is preferably greater than 10%. The sheet resistance of the cathode is preferably several hundreds Ω/ or less. Although depending upon materials, the film thickness of the cathode is generally 10 nm to 1 μm, preferably 50 to 200 nm.

For effectively transmitting light from the organic light-emitting layer, at least one of the above anode and cathode is preferably formed of a transparent or semitransparent material.

When the organic light-emitting layer of the organic EL device of the present invention is formed from the silanamine derivative and other substance or formed from only a substance other than the silanamine derivative, the other substance can be selected, for example, from compounds which are excellent in formability of thin film, such as polycyclic fused aromatic compounds, benzooxazole-, benzothiazole- and benzoimidazole-fluorescent brighteners, metal chelated oxanoid compounds, and distyrylbenzene compounds.

Specific examples of the above polycyclic fused aromatic compounds include fused-ring light-emitting substances each containing an anthracene, naphthalene, phenanthrene, pyrene, chrysene or perylene skeleton and other fused-ring light-emitting substances having 8 to 20, preferably, 8 fused rings.

Examples of the above benzooxazole-, benzothiazole- and benzoimidazole-fluorescent brighteners include those disclosed in JP-A-59-194393. Typical examples thereof include benzooxazole-fluorescent brighteners such as 2,5-his (5,7-di-tert-pentyl-2-benzooxazolyl)-1,3,4-thiaziazole, 4,4'-bis(5,7-tert-pentyl-2-benzooxazolyl)stilbene. 4.4'-bis(5,7-di-(2-methyl-2-butyl)-2-benzooxazolyl)stilbene, 2,5-bis(5,7-di-tert-pentyl-2-benzooxazolyl)thiophene. 2,5-bis(5-(α, α-dimethylbenzyl)-2-benzooxazolyl)thiophene, 2,5-bis(5,7-di-(2-methyl-2-butyl)-2-benzooxazolyl) -3,4-diphenylthiophene, 2,5-bis(5-methyl-2-benzooxazolyl)thiophene, 4,4'-bis(2-benzooxazolyl)biphenyl, 5-methyl-2-(2-(4-(5-methyl-2-benzooxazolyl)phenyl)vinyl)benzooxazole and 2-(2-(4-chlorophenylvinyl)naptho (1,2-d)oxazole; benzothiazolefluorescent brighteners such as 2,2'-(p-phenylenedivinylene)bisbenzothiazole; and benzoimidazole-fluorescent brighteners such as 2-(2-(4-(2-benzoimidazolyl)phenyl)vinyl)benzoimidazole and 2-(2-(4-carboxyphenyl)vinyl)benzoimidazole.

Examples of the above metal chelated oxanoid compounds include those disclosed in JP-A-53-295695. Typical examples thereof include 8-hydroxyquinoline-containing metal complexes; such as tris(8-quinolinol)aluminum, bis(8-quinolinol), magnesium, bis(benzo(f)-8-quinolinol)zinc, bis(2-methyl-8-quinolinolate)aluminum oxide, tris(8-quinolinol)indium, tris(5-methyl-8-quinolinol)aluminum, 8-qunioliniollithium, tris(5-chloro-8-quniolinol)gallium, bis(5-chloro-8-quinolinol)calcium and poly(zinc(II)-bis(8-hydroxy-5-quinolinonyl)methane): and dilithium epindolidione.

Examples of the above distyrylbenzene compounds include those disclosed in European Patent 0 373 582. Typical examples thereof include 1,4-bis(2-methylstyryl)benzene, 1,4-bis(3-methylstyryl)benzene, 1,4-bis(4-methylstyryl)benzene, distyrylbenzene, 1,4-bis(2-ethylstyryl)benzene, 1,4-bis(3-ethylstyryl)benzene, 1,4bis-(2-methylstyryl)-2-methylbenzene and 1,4-bis(2-methylstyryl)-2-ethylbenzene.

Further, the material for the organic light-emitting layer can be selected from distyrylpyrazine derivatives disclosed in JP-A-2-252793. Typical examples of the distyrylpyrazine derivatives include 2,5-bis(4-methylstyryl)pyrazine, 2,5-bis(4-ethylstyryl)pyrazine, 2,5-bis[2-(1-naphthyl)vinyl]pyrazine, 2,5-bis(4-methoxystyryl)pyrazine and 2,5-bis[2-(1-pyrenyl)vinyl]pyrazine.

Further, the material for the organic light-emitting layer can be selected from dimethylidene derivatives disclosed in European Patent 0 388 768 and JP-A-3-231970. Specific examples of the dimethylidene derivatives include 1,4-phenylenedimethylidene, 4,4'-phenylenedimethylidene, 2,5-xylylenedimethylidene, 2,6-naphthylenedimethylidene, 1,4-biphenylenedimethylidene, 1,4-p-terphenylenedimethylidene, 9,10-anthracen-diyldimethylide, 4,4'-(2,2-di-tert-butylphenylvinyl )-biphenyl, 4,4'-(2,2-diphenylvinyl)biphenyl and derivatives of these.

Furthermore, the material for the organic light-emitting layer can be also selected from coumarin derivatives disclosed in JP-A-2-191694, perylene derivatives disclosed in JP-A-2-196885, naphthalene derivatives disclosed in JP-A-2-255789, phthaloperinone derivatives disclosed in JP-A-2-289676 and JP-A-2-88689 and styrylamine derivatives disclosed in, IP-A-2-250292.

The material for the organic light-emitting layer can be suitably selected depending on a desired emitted color, characteristics and the like.

The organic light-emitting layer of the organic EL device of the present invention may be formed from a mixture prepared by incorporating a luminescent substance into a base material, as is disclosed in U.S. Pat. No. 4,769, 292. In this case, the base material may be the silanamine derivative, an organic light-emitting layer material other than the silanamine derivative or a mixture of these. When the organic light-emitting layer is formed from a mixture prepared by incorporating a luminescent substance into the base material, the amount of the luminescent substance is preferably several mol % or less. The luminescent substance, emitting light in response: to recombination of electron and hole, partly functions for light emission.

The material for forming the organic light-emitting layer may be selected from compounds having no formability of thin film such as 1,4-diphenyl-1,3-butadiene, 1,1,4,4-tetraphenyl-1,3-butadiene and tetraphenylcyclopentadiene. However, an organic EL device having the; organic light-emitting layer formed therefrom has a defect that the life of the device is short.

The hole-conducting layer optionally formed in the organic EL device of the present invention may be a layer containing the silanamine derivative or a layer containing no silanamine derivative as far as the organic light-emitting layer contains the silanamine derivative. The material for forming the hole-conducting layer, other than the silanamine derivative, can be selected from a variety of substances conventionally used for forming the hole-conducting layer of an organic EL device.

When a layer containing the silanamine derivative is formed as the hole-conducting layer optionally formed in the organic EL device of the present invention, this hole-conducting layer may have the structure of a single layer formed from the silanamine derivative; a multi-layer formed of a layer element of the silanamine derivative and a layer element of a substance conventionally used for forming a hole-conducting layer of an organic EL device; or a single or multi-layer containing a layer formed from a mixture of the silanamine derivative and a substance conventionally used for forming a hole-conducting layer of an organic EL device. In this case, the layer structure is preferably a structure of a single layer formed from the silanamine derivative alone, or a multi-layer formed of a layer formed from the silanamine derivative and a layer formed from a porphyrin compound (disclosed in JP-A-65-295695) or a p-type thiophene-containing oligomer which is an organic semi-conductive oligomer.

Typical examples of the above porphyrin compound include porphine, 5,10,15,20-tetraphenyl-21H, 23H-porphine copper (II), 5,10,15, 20-tetraphenyl -21H, 25H-porphine zinc (II), 5,10,15, 20-tetrakis(pentafluorophenyl)-21H, 23H-porphine, silicon phthalocyanine oxide, aluminum phthalocyanine chloride, phthalocyanine (metal-free), dilithium phthalocyanine, copper tetramethylphthalocyanine, copper phthalocyanine, chromium phthalocyanine, zinc phthalocyanine, lead phthalocyanine, titanium phthalocyanine, magnesium phthalocyanine and copper octylmethylphthal ocyanine.

As the above p-type thiophene-containing oligomer particularly preferred is an organic semi-conductive oligomer of the following formula,

wherein k=1, 2 or 3, m=1, 2 or 3, n=1, 2 or 3, k+m+n≧5, and each of $R^1$ $R^2$ and $R^3$ is independently an alkyl group having 1 to 10 carbon atoms, an alkoxy group having 1 to 10 carbon atoms or cyclohexyl.

The electron-injecting layer (injected electron-conducting layer) optionally, formed in the organic EL device of the present invention has a function, in principle, of transmitting electrons injected by the cathode to the organic light-emitting layer. The material therefor can be freely selected from known electron-transmitting compounds.

Specific examples of the electron-transmitting compound preferably includes compounds of the following formula (1) to (5).

(1)

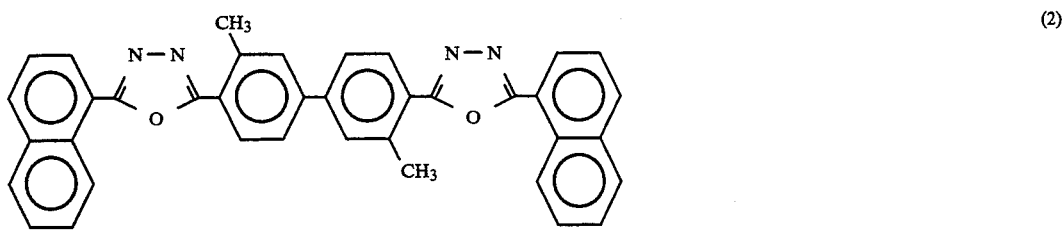

(2)

(3)

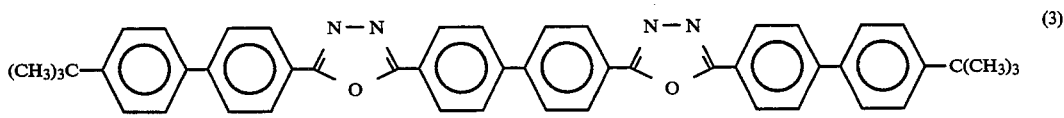

(4)

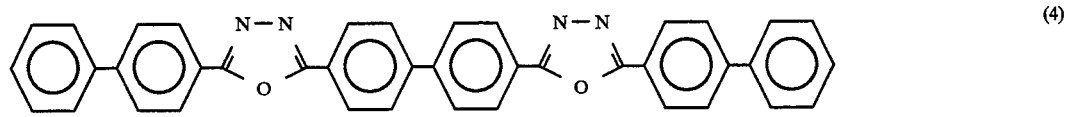

(5)

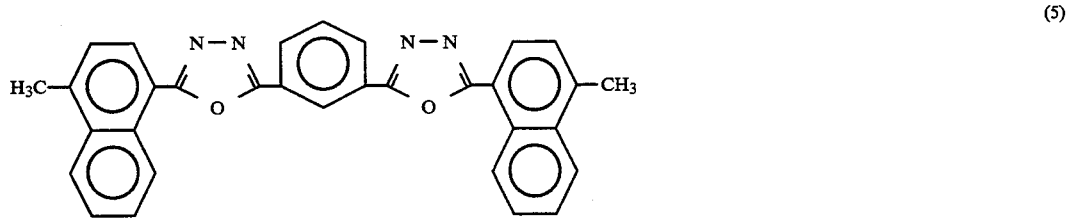

The electron-injecting layer is a layer having the ability to inject, conduct or hinder electrons, and in addition to the above-described compounds (1) to (5), the material therefor can be formed from crystalline or amorphous Si-, SiC- and CdS-containing materials.

In addition to the above anode, cathode, organic light-emitting layer, optionally formed hole-conducting layer and optionally formed electron-injecting layer, the organic EL device of the present invention may have a layer to improve interlayer adhesion. Specific examples of the material for forming the above layer, i.e., a layer for improvement of the adhesion between the organic light-emitting layer and the cathode, quinolinol metal complexes such as tris(8-quinolinol)aluminum and tris(8-quinol inol) indium.

The above-explained organic EL device of the present invention can be produced, for example, as follows depending upon its constitutions.

(A) Production of organic EL device having constitution of anode/organic light-emitting layer(containing silanamine derivative)/cathode —1—

First, an anode is produced on a proper substrate by forming a thin film having a thickness off 1 μm or less, preferably 10 to 200 nm from a desired electrode substance, e.g., an anode substance by a vapor-deposition or sputtering method. Then, an organic light-emitting layer is formed on the anode by forming a thin film of the silanamine derivative of the formula (I). The thin film of the silanamine derivative can be formed by any one of a vacuum vapor-deposition method, a spin coating method and a casting method, while a vacuum vapor-deposition method is preferred since a uniform film can be easily formed and since pin holes are hardly formed.

The conditions for the vapor-deposition for forming a thin film of the silanamine derivative differ depending upon the kind of tile silanamine derivative and the crystal structure and associative structure of the intended organic light-emitting layer. In general, preferred conditions are as follows. The temperature for heating a boat is 50° to 400° C., the vacuum degree is $10^{-5}$ to $10^{-3}$ Pa. the vapor deposition rate is 0.01 to 50 nm/sec, the substrate temperature is $-50°$ to $+300°$ C. and the film thickness is 5 nm to 5 μm.

After the organic light-emitting layer is formed, a cathode is produced on the organic light-emitting layer by forming a thin film having a thickness of 1 μm or less, preferably 10 to 200 nm from a cathode substance by a vapor-deposition or sputtering method, whereby the intended organic EL device is obtained. This organic EL device can be also produced by reversing the production steps, i.e., in the order of cathode/organic light-emitting layer/anode.

(B) Production of organic EL device having constitution of anode/organic light-emitting layer (containing silanamine derivative)/cathode —2—

First, an anode is formed on a proper substrate in the same manner as in the above (A). Then, an organic light-emitting layer is formed on the anode by applying a solution containing a hole-conducting layer material, an organic light-emitting layer material, an electron-injecting layer material and a binder (polyvinyl carbazole, or the like) or by an immersion method using this solution.

Then, a cathode is produced by forming a thin film of a cathode material on the organic light-emitting layer in the same manner as in the above (A), whereby the intended organic EL device is obtained.

In addition, the organic light-emitting layer may be of a multi-layer structure obtained by forming a thin film of a desired organic light-emitting layer material on the above-formed layer by a vacuum vapor-deposition method or other method. Further, the organic light-emitting layer nay be formed by vapor-depositing an organic light-emitting layer material together with a hole-conducting layer material and an electron-injecting layer material.

(C) Production of organic EL device having constitution of anode/hole-conducting layer (containing silanamine derivative)/organic light-emitting layer/cathode.

First, an anode is formed on a proper substrate in the same manner as in the above (A). Then, a hole-conducting layer is produced on the anode by forming a thin film of the silanamine derivative of the formula (I). This hole-conducting layer can be formed in the same manner as in the formation of the organic-light-emitting layer (containing the silanamine derivative) in the above (A).

Then, an organic light-emitting layer is formed on the hole-conducting layer from a desired organic light-emitting layer material. The organic light-emitting layer can be produced by forming a thin film of an organic light-emitting layer material by any one of a vacuum vapor-deposition method, a spin coating method and a casting method. A vapor-deposition method is preferred since a uniform film can be easily formed and since pin holes are hardly formed.

Then, a cathode is produced by forming a thin film from a cathode substance in the same manner as in the above (A), whereby the intended organic EL device is obtained. This organic EL device can be also produced by reversing the above production steps, i.e., in the order of cathode/organic light-emitting layer/hole-conducting layer/anode.

(D) Production of organic EL device having constitution off anode/hole-conducting layer(containing silanamine derivative)/organic light-emitting layer/electron-injection layer/cathode.

First, an anode, a hole-conducting layer (containing the silanamine derivative) and an organic light-emitting layer are formed on a proper substrate in the same manner as in the above (C).

After the formation of the organic light-emitting layer, an electron-injecting layer is produced on the organic light-emitting layer by forming a thin film having a thickness of 1 μm or less, preferably 5 to 100 nm from an electron-injection layer material by a vapor-deposition method or a sputtering method.

Then, a cathode is produced on the electron-injecting layer from a cathode substance in the same manner as in the above (C), whereby the intended organic EL device is obtained. This organic EL device can be also produced by reversing the above production steps, i.e., in the order of cathode/electron-injecting layer/organic light-emitting layer/anode.

The organic EL device of the present invention, produced by any one of the above methods, emits light by applying a direct current of 5 to 40 V with the anode being + (plus) and the cathode being — (minus). When a voltage is applied with the polarities being reversed, no current occurs and no light emission occurs. When a voltage with an alternate current is applied, light is emitted only when the anode is + (plus) and the cathode is — (minus). When a voltage with an alternate current is applied, the alternate current may have any waveform.

In the organic EL device of the present invention, at least one layer of the single or plural compound layer(s) contains the silanamine derivative of the formula (I). And, the ionization potential of this silanamine derivative is as low as 5.5 to 5.6 eV. Therefore, the organic EL device of the present invention can be actuated with a low voltage.

Further, a thin film formed from the silanamine derivative of the formula (I) undergoes recrystallization with time much slower than any thin film of a conventional amino compound (e.g. TPD). For this reason, the present invention makes it easier to obtain an organic EL device which is less deteriorated in life time of the device than any organic EL device using an amino compound.

The present invention will be detailed by reference to Examples.

Example 1

Production of Silane Derivative

A three-necked flask was flushed with argon and charged with 2.00 g (5.95 mmol) of N,N'-diphenyl-benzidine [diarylamine shown as (1) in Table 9, supplied by Tokyo Kasei K.K.]. This N,N'-diphenyl-benzidine was dissolved in 200 ml of THF distilled with a sodium wire under an argon atmosphere, and added to the resulting mixture was 10 ml of a solution of n-butyllithium (about 16 mmol) in hexane. The mixture was heated at 50° C. For 0.5 hour and cooled, and then a solution of 3.98 g (13.5 mmol) of triphenylchlorosilane (halogenated silane shown as (I) in Table 12, supplied by Shin-Etsu Chemical Co., Ltd.) in 100 ml of THF (distilled with a sodium wire under an argon atmosphere) was slowly added dropwise through a funnel. The resultant mixture was allowed to react at room temperature, and after 18 hours, 100 ml of water was added to terminate the reaction.

The above-obtained reaction mixture was subjected to extraction with 200 ml of methylene chloride twice, and the extract was dried over anhydrous sodium sulfate. The solvent was evaporated off by means of an evaporator to give a white crystal. This white crystal was purified by column chromatography using Wako Gel C-200 (trade name, silica gel type solid support, supplied by Hiroshima Wako Pure Chemical Industries, Ltd.) as a solid support and toluene as a developer, to give 0.79 g of a white crystal.

The above-obtained white crystal had a melting point of 209° C., and was measured for NMR (H: 400 MHz, THF-d8) to show a result as shown in FIG. 1.

The white crystal was also measured for FD-MS (field desorption mass spectroscopy) to show a mass spectral parent peak of 852 as against $C_{60}H_{48}N_2Si_2=852$. It was further measured for IR (infrared absorption spectrum) to show absorption at 1,600, 1,500, 1,280 and 900 (cm$^{-1}$).

These results show that tile above-obtained white crystal was a silanamine derivative (to be abbreviated as "Sil-1" hereinafter) shown as (1) in Table 1 (yield 16%).

Example 2

Production of Silanamine Derivative 2.00 g (6.92 mmol) of N,N'-diphenyl-1,4-benzenediamine (diarylamine shown as (2) in Table 9, supplied by Kanto Kagaku K. K.), 10 ml of a solution of n-butyllithium (about 16 mmol) in hexane and 4.10 g (13.6 mmol) of triphenylchlorosilane [halogenated silane shown as (1) in Table 12, supplied by Shin-Etsu Chemical Co. Ltd.) were allowed to react in the same manner as in Example 1.

After the reaction finished, the crystal was obtained by filtration, washed with a hot pyridine solution and dried to give 0.88 g of a white crystal.

The above white crystal had a melting point of 300° C. or higher. It was measured for FD-MS to show a mass spectral parent peak of 776 as against $C_{54}H_{44}N_2Si_2=776$. It was further measured for IR to show absorption at 1,600, 1,500, 1,280 and 900 (cm$^{-1}$).

These results show that the above-obtained white crystal was a silanamine derivative (to be abbreviated as "Sil-2" hereinafter) shown as (2) in Table 1 (yield 16%).

Example 3

Production of Silanamine Derivative b 2.02 g (5.61 mmol) of N,N'-di-(2-naphthyl)-1,4-benzenediamine (diarylamine shown as (3) in Table 9, supplied by Kanto Kagaku K. K.), 10 ml of a solution of n-butyllithium (about 16 mmol) in hexane and 3.98 g (13.5 mmol) of triphenylchlorosilane [halogenated silane shown as (1) in Table 12, supplied by Shin-Etsu Chemical Co. Ltd.) were allowed to react in the same manner as in Example 1.

After the reaction finished, the crystal was obtained by filtration, washed with a hot pyridine solution and dried to give 1.39 g of a white crystal.

The above white crystal had a melting point of 300° C. or higher. It was measured for FD-MS to show a mass spectral parent peak of 876 as against $C_{62}H_{48}N_2Si_2=876$. It was further measured for IR to show absorption at 1,600, 1,490, 1,280 and 920 (cm$^{-1}$).

These results show that the above-obtained white crystal was a silanamine derivative (to be abbreviated as "Sil-3" hereinafter) shown as (3) in Table 1 (yield 28%).

Example 4

Production of Silanamine Derivative (1) Production of Diarylamine

A diarylamine as a starting material was produced as follows.

A reactor was flushed with argon and charged with 12.24 g (82.1 mmol) of p-tolylacetanilide (supplied by Hiroshima Wako Pure Chemicals Industries, Ltd.), 10.03 g (32.1 mmol) of 4,4'-dibromobiphenyl (supplied by Hiroshima Wako Pure Chemical Industries, Ltd.), 20.22 g (145 mmol) of anhydrous potassium carbonate, 1.0 g (15.6 mmol) of a copper powder and 0.12 g (0.9 mmol) of iodine, and the mixture was suspended in 200 ml of DMSO and allowed to react at 200° C. for 48 hours. Then, a solution of 20 g of KOH in 50 ml of water was added, and the hydrolysis was carried out at 80° C. for 5 hours.

The reaction mixture was filtered to remove inorganic substances and subjected to extraction with ethyl acetate, and the solvent was evaporated off with an evaporator. Then, the residue was purified by column chromatography to give 7.01 g of a white crystal.

The above-obtained white crystal had a melting point of 252° to 255° C. The results of NMR, measurement thereof were as follows: δ (ppm); 7.59–7.40 (dd, SH), 7.10–7.02 (dd, SH), 3,49 (s, 6H), 2.32 (s, 2H). The above white crystal was further measured for FD-MS to show a mass spectral parent peak of 384 as against $C_{26}H_{24}N_2=364$.

These results show that the above-obtained white crystal was diarylamine[N,N'-di-(p-tolyl)benzidine]-shown as (4) in Table 9 (yield 60%).

(2) Production of Silanamine Derivative 2.00 g (5.49 mmol) of the N,N'-di-(p-tolyl)benzidine obtained in the above (1), 10 ml of a solution of n-butyllithium (about 16 mmol) in hexane and 4.02 g (13.7 mmol) of triphenylchlorosilane [halogenated silane shown as (1) in Table 12, supplied by Shin-Etsu Chemical Co., Ltd.] were allowed to react in the same manner as in Example 1.

After the reaction finished, the reaction mixture was subjected to extraction with a solvent and purification by column chromatography in the same manner as in Example 1 to give 1.01 g of a white crystal.

The above white crystal had a melting point of 300° C. or higher. It was measured for FD-MS to show a mass spectral parent peak of 880 as against $C_{82}H_{52}N_2Si_2=880$. It was further measured for IR to show absorption at 1,600, 1,500, 1,280 and 910 (cm$^{-1}$).

These results show that the above-obtained white crystal was a silanamine derivative (to be abbreviated as "Sil-4" hereinafter) shown as (4) in Table 1 (yield 21%).

Example 5

(1) Production of Diarylamine

A diarylamine as a starting material was produced as follows.

5.01 g (20.9 mmol) of 3,3′,5,5′-tetramethylbenzidine (supplied by Tokyo Kasei K.K.) and 8.0 g (60 mmol) of acetic arthydride were dissolved in 50 ml of methylene chloride, and one drop off concentrated sulfuric acid was added. Thereafter, the mixture was stirred at room temperature for 8 hours, and then subjected to extraction with methylene chloride.

After the extraction, the solvent and acetic arthydride were evaporated off under reduced pressure, and the residue was purified by column chromatography. The resultant purified product was treated in the same manner as in Example 4 (1) except that the 4,4′-dibromobiphenyl was replaced with 6.0 g (38 mmol) of benzene bromide (supplied by Tokyo Kasei K. K.), to give 1.44 g of a white crystal.

The above white crystal was measured for FD-MS to show a mass spectral parent peak of 392 as against $C_{28}H_{28}N_2=392$.

The above result shows that the above-obtained white crystal was diarylamine[N,N′-diphenyl-3,3′,5,5′-tetramethylbenzidine] shown as (5) in Table 9 (yield 18%).

(2) Production of Silasamine Derivative 2.00 g (5. 10 mmol) off the N,N′-diphenyl -3,3′,5,5′-tetramethylbenzidine obtained in the above (1), 10 ml of a solution of n-butyllithium (about 16 mmol) in hexane and 3.98 g (13.5 mmol) of triphenylchlorosilane [halogenated silane shown as (1) in Table 12, supplied by Shin-Etsu Chemical Co., Ltd.] were allowed to react in the same manner as in Example 1.

After the reaction finished, the reaction mixture was subjected to extraction with a solvent and purification by column chromatography in the same manner as in Example to give 0.37 g of a pinkish crystal.

The above pinkish crystal had a melting point of 300° C. or higher. It was measured for FD-MS to show a mass spectral parent peak of 908 as against $C_{68}H_{24}N_2Si_2=908$. It was further measured for IR to show absorption at 1,590, 1,500, 1,300 and 900 (cm$^{-1}$).

These results show that the above-obtained pinkish crystal was a silasamine derivative (to be abbreviated as "Sil-5" hereinafter) shown as (5) in Table 1 (yield 8%).

Example 6

Production of Silanamine Derivative 2.01 g (5.98 mmol) of the N,N′-diphenyl-benzidine [diarylamine shown as (1) in Table 9, supplied by Tokyo Kasei K. K.], 10 ml of a solution off n-butyllithium (about mmol) in hexane and 5.01 g (14.9 mmol) of tri(p-tolyl)chlorosilane [halogenated silane shown as (2) in Table 12, supplied by Shin-Etsu Chemical Co., Ltd.] were allowed to react in the same manner as in Example 1.

After the reaction finished, the reaction mixture was subjected to extraction with a solvent and purification by column chromatography in the same manner as in Example 1 to give 1.40 g of a white crystal.

The above white crystal had a melting point of 300° C. or higher. It was measured for FD-MS to show a mass spectral parent peak of 936 as against $C_{66}H_{60}N_2Si_2=935$. It was further measured for IR to show absorption at 1,600, 1,500, 1,280 and 900 (cm$^{-1}$).

These results show that the above-obtained pinkish crystal was a silanamine derivative (to be abbreviated as "Sil-6" hereinafter) shown as (6) in Table 1 (yield 25%).

Example 7

Production of Silanamine Derivative (1) Production of Diarylamine

Diarylamine as a starting material was produced as follows.

A reactor was flushed with argon and charged with 15.80 g (85.4 mmol) of 1-acetylaminonaphthalene (supplied by Kanto Kagaku K. K.), 13.51 g (33.3 mmol) of 4,4′-diiododiphenyl (supplied by Hiroshima Wako Pure Chemical industries, Ltd.), 14.98 g (109 mmol) of anhydrous calcium carbonate and 1.0 g of a copper powder, and the mixture was suspended in 200 ml of DMSO and allowed to react at 200° C. for 48 hours.

Then, a solution of 6.4 g of potassium hydroxide in 50 ml of water was added to the above-obtained reaction mixture, and 100 ml of THF was added. The hydrolysis was carried out at 80° C. for 5 hours.

The reaction mixture was filtered to remove inorganic substances and subjected to extraction with ethyl acetate, and the solvent was evaporated off with an evaporator. Then, the residue was purified by column chromatography to give 3.56 g of a white crystal.

The above-obtained white crystal had a melting point of 246° to 248° C. The results of NMR measurement thereof were as follows: δ (ppm) 8.10–7.82 (m, 41t), 7.58–7.36 (m, 16H ), 7.08–6.99 (m, 2H), 2.36 (s, 2H ). The above white crystal was further measured for FD-MS to show a mass spectral parent peak of 436 as against $C_{32}H_{24}N_2=436$.

These results show that the above-obtained white crystal was diarylamine [N,N′-di-(1-naphthyl)benzidine] shown as (34) in Table 11 (yield 25%).

(2) Production of Silanamine Derivative 2.03 g (4.66 mmol) of the N,N′-di-(1-naphthyl)benzidine obtained in the above (1), 10 ml of a solution of n-butyllithium (about 16 mmol) in hexane and 3.87 g (13.1 mmol) of triphenylchlorosilane [halogenated silane shown as (1) in Table 12, supplied by Shin-Etsu Chemical Co., Ltd.] were allowed to react in the same manner as in Example 1.

After the reaction finished, the reaction mixture was subjected to extraction with a solvent and purification by column chromatography in the same manner as in Example 1 to give 3.28 g of a white crystal.

The above white crystal had a melting point of 300° C. or higher. It was measured for FD-MS to show a mass spectral parent peak of 952 as against $C_{68}H_{52}N_2Si_2$=952. It was further measured for IR to show absorption at 1,600, 1,500, 1,280 and 890 (cm$^{-1}$).

These results show that the above-obtained white crystal was a silanamine derivative ("to be abbreviated as "Sil-7" hereinafter) shown as (43) in Table 8 (yield 74%).

Example 8

(1) Production of Diarylamine

Diarylamine as a starting material was produced as follows.

5.0 g (19 mmol) of 4,4'-diaminoterphenylene was charged into a reactor and dissolved in 500 ml of THF, and 13 ml of acetic anhydride was added slowly. The mixture was allowed to react at room temperature for 12 hours, the reaction mixture was filtered and washed with THF to give 10.83 g of a white crystal.

A reactor was flushed with argon and charged with 10.02 g (29.0 mmol) of the above crystal 14.92 g (76.1 mmol) of iodobenzene (supplied by Tokyo Kasei K.K.), 14.78 g (107 mmol) of anhydrous potassium carbonate and 1.0 g of a copper powder, and the mixture was suspended in 200 ml of DMSO and allowed to react at 200° C. For 48 hours.

Then, a solution of 21 g of potassium hydroxide in 50 ml of water was added to the above-obtained reaction mixture, and after 100 ml of THF was added, the hydrolysis was carried out at 80° C. for 5 hours.

After the reaction finished, inorganic substances were removed by filtration, and the residue was subjected to extraction with ethyl acetate. Then, the solvent was evaporated off with an evaporator. The residue was purified by column chromatography to give 5.62 g of a white crystal.

The above-obtained white crystal had a melting point of 238° to 240° C. The results of NMR measurement thereof were as follows: δ (ppm) 7.62–7.46 (m, 10H), 7.29 –6.94 (m, 12H), 2.10 (s, 2H). The above white crystal was further measured for FD-MS to show a mass spectral parent peak off 412 as against $C_{30}H_{24}N_2$=412.

These results show that the above-obtained white crystal was diarylamine [N,N'-di-diphenyl-4,4'-diaminoterphenylene] shown as (35) in Table 11 (yield 4 V %).

(2) Production of Silanamine Derivative 2.30 g (5.58 mmol) of the N,N'-diphenyl -4,4'-diaminoterphenylene obtained in the above (1), 10 ml of a solution of n-butyllithium (about 16 mmol) in hexane and 4.29 g (14.5 mmol) of triphenylchlorosilane [halogenated silane shown as (1) in Table 12. supplied by Shin-Etsu Chemical Co., Ltd.] were allowed to react in the same manner as in Example 1.

After the reaction finished, the reaction mixture was subjected to extraction with a solvent and purification by column chromatography in the same manner as in Example 1 to give 0.38 g of a white crystal.

The above white crystal had a melting point of 300° C. or higher. It was measured for FD-MS to show a mass spectral parent peak of 928 as against $C_{66}H_{52}N_2Si_2$=928. It was further measured for IR to show absorption at 1,600, 1,500, 1,280 and 900 (cm$^{-1}$).

These results show that the above-obtained white crystal was a silanamine derivative (to be abbreviated as "Sil-8" hereinafter) shown as (44) in Table 8 (yield 7%).

Example 9

Production of Silanamine Derivative

(1) Production Of Diarylamine

Diarylamine as a starting material was produced as follows.

A reactor was flushed with argon and charged with 15.04 g (101 mmol) off m-acetotoluide (supplied by Hiroshima Wako Pure Chemical Industries, Ltd.), 15.71 (38.7 mmol) of 4,4'-diiododiphenyl (supplied by Hiroshima Wako Pure Chemical Industries, Ltd.) 20.31 g (147 mmol) of anhydrous potassium carbonate and 1.0 g off a copper powder, and the mixture was suspended in 200 ml of DMSO and allowed to react at 200° C. for 48 hours.

Then, a solution of 20 g of potassium hydroxide in 50 ml of water was added to the above-obtained react ion mixture, and after 100 ml of THF was added, the hydrolysis was carried out at 80° C. for 5 hours.

After the reaction finished, inorganic substances were removed by filtration, and the residue was subjected to extraction with ethyl acetate. Then, the solvent was evaporated off with an evaporator. The residue was purified by column chromatography to give 5.11 g of a white crystal.

The above-obtained white crystal had a melting point of 155° to 157° C. The results of NMR measurement thereof were as follows: δ (ppm) 7.80–7.04 (m, 16H), 2.52 (s, 2H), 2.32 (s, 6H). The above white crystal was further measured for FD-MS to show a mass spectral parent peak off 364 as against $C_{26}H_{24}N_2$=364.

These results show that the above-obtained white crystal was diarylamine[N,N'-di-(m-tolyl)-benzidine] shown as (12) in Table 10 (yield 36% ).

(2) Production of Silanamine Derivative 2.17 g (5.96 mmol) of the N,N'-di-(m-tolyl) benzidine obtained in the above (1), 10 ml of a solution of n-butyllithium (about 16 mmol) in hexane and 4.35 g (14.7 mmol) of triphenylchlorosilane [halogenated silane shown as (1) in Table 12, supplied by Shin-Etsu Chemical Co., Ltd.] were allowed to react in the same manner as in Example 1.

After the reaction finished, the reaction mixture was subjected to extraction with a solvent and purification by column chromatography in the same manner as in Example 1 to give 2.03 g of a white crystal.

The above white crystal had a melting point of 300° C. or higher. I t was measured for FD-MS to show a mass spectral parent peak of 850 as against $C_{62}H_{52}N_2Si_2$=880. It was further measured for IR to show absorption at 1,600, 1,500, 1,280 and 900 (cm$^{-1}$).

These results show that the above-obtained white crystal was a silanamine derivative (to be abbreviated as "Sil-9" hereinafter) shown as (13) in Table 3 (yield 39%).

Measurement of Ionization Potential

Each of the silanamine derivatives obtained Examples 1 to 9 was measured for an ionization potential with a UV-photoelectron spectrometer AC-1 (trade name ) supplied by Riken Keiki K. K.

For comparison, hexaphenylcyclodisilazane as one of cyclosilanes and TPD [N,N'-bis-(m-tolyl)-N,N'-diphenyl-1,1'-biphenyl] as one of amino compounds were measured for ionization potentials in the same manner as above.

Table 13 shows the results.

TABLE 13

| | Ionization potential |
|---|---|
| Silanamine derivative of Example 1 | 5.6 eV |
| Silanamine derivative of Example 2 | 5.5 eV |
| Silanamine derivative of Example 3 | 5.5 eV |
| Silanamine derivative of Example 4 | 5.5 eV |
| Silanamine derivative of Example 5 | 5.6 eV |
| Silanamine derivative of Example 6 | 5.5 eV |
| Silanamine derivative of Example 7 | 5.5 eV |
| Silanamine derivative of Example 8 | 5.6 eV |
| Silanamine derivative of Example 9 | 5.5 eV |
| Hexaphenylcyclodisilazane | 5.7 eV |
| TPD | 5.5 eV |

As shown in Table 13, the silanamine derivatives obtained in Examples 1 to 9 had an ionization potential 5.5 to 5.6 eV, which values are equivalent to, or slightly higher than, that of TPD, but are lower than the 5.7 eV ionization potential of hexaphenylcyclodisilazane.

The above data shows that the silanamine derivatives obtained in Examples 1 to 9 have a characteristic feature in that holes can be more easily injected into these silanamine derivatives than into hexaphenylcyclodisilazane.

Comparative Example 1

Production of 4,4'-di-tert-butyltriphenylamine 22.5 g (0.08 tool) of 4,4'-di-tert-butyldiphenylamine, 32.6 g (0.16 mol) off iodobenzene, 16.6 g (0.12 mol) of anhydrous calcium carbonate and 0.5 g (8 mmol) of a copper powder were mixed, and the mixture was allowed to react in DMSO as a solvent at 200° to 230° C. For 5 hours.

After the reaction finished, 200 ml of toluene was added in which a formed product was dissolved but inorganic salts remained as a solid. Therefore, differing from the cases in Examples 1 to 9, it was difficult to purify the product. Further, it was required to dispose of a waste solution of copper salt.

Example 10

Production of Organic EL Device

A plate prepared by forming an ITO film (corresponding to an anode) having a thickness of 100 nm on glass substrate [25 mm×75 mm×1 mm, supplied by HOYA Corp. under the trade name of "NA 40"] was used as a transparent substrate. This transparent substrate was subjected to ultrasonic washing in isopropyl alcohol for 5 minutes, then blown by dry nitrogen, dried and further washed with a UV ozone washing apparatus (trade name: UV300, supplied by Sacore International Co., Ltd.) for 10 minutes.

The so-washed transparent substrate was set in a substrate holder of a vacuum vapor-deposition apparatus (supplied by Nippon Shinku Gijutsu K. K.), and the vacuum chamber was evacuated until $1 \times 10^{-4}$ Pa. Before the evacuation, a molybdenum resistive-heating boat in which 200 mg of the silanamine derivative (Sil-1) obtained in Example 1 was placed, a molybdenum resistive-heating boat in which 4,4'-bis-(2,2-diphenylvinyl)-1,1'-biphenyl (to be abbreviated as DPVBi hereinafter) as a dimethylidene-type light-emitting material was placed and a molybdenum resistive-heating boat in which 200 mg of tris(8-quinolinol) aluminum (to be abbreviated as Alq hereinafter) as an electron-conducting, adhesive-improver substance was placed were respectively set at electricity-applying terminal beds.

After the evacuation, the boat with Sil-1 in it was heated up to 270° C. to vapor-deposit Sil-1 on the ITO film at a deposition rate of 0.4 to 0.6 nm/sec, whereby a Sil-1 layer (corresponding to a hole-conducting layer) having a thickness of 60 nm was formed.

Then, the boat with DPVBi in it was heated to vapor-deposit DPVBi on the Sil-1 layer at a deposition rate of 0.4 to 0.6 nm/sec, whereby a DPVBi layer (corresponding to an organic light-emitting layer) having a thickness of 40 nm was formed.

The boat with Alq in it was heated to vapor-deposit Alq on the DPVBi layer at a deposition rate of 0.1 to 0.3 nm/sec, whereby an Alq layer (corresponding to an adhesive improver layer) having a thickness of 20 nm was formed.

Thereafter, the vacuum chamber was opened, and a molybdenum boat with magnesium in it and a tungsten filament boat with silver in it were set at electricity-applying terminal beds. Further, a mask for vapor deposition was set on the above-produced glass substrate/Sil-1 layer/DPVBi layer/Alq layer.

The vacuum chamber was evacuated until $1 \times 10^{-4}$, and electricity was applied to the filament boat with silver in it to vapor-deposit silver at a deposition rate off 0.09 to 0.1 nm/sec, and at the same, electricity was applied to the boat with magnesium in it to vapor-deposit magnesium at a deposition rate of 1.4 to 1.7 nm/sec. By this simultaneous two-element vapor deposition, a magnesium-silver layer (corresponding to a cathode) having a thickness of 150 nm was formed on the Alq layer.

All the layers including the cathode were formed on the glass plate as above, whereby an organic EL device was obtained.

When a voltage of 9.5 V was applied to the above-obtained organic EL device with the magnesium-silver layer being as a cathode and the ITO film being as an anode, a blue light emission at 114 cd/m² was observed. Table 14 shows the current density, brightness, luminous efficiency and emitted light color in this case. The maximum brightness of emitted light from this organic EL device was 1,000 cd/m².

Example 11

Production of Organic EL Device

An organic EL device was obtained in the same manner as in Example 10 except that copper phthalocyanine (to be abbreviated as CuPc hereinafter) and Sil-1 were used as hole-conducting layer materials.

In addition, the hole-conducting layer was formed in the following manner so as to have a two-layer structure. A molybdenum boat with CuPc in it was heated to vapor-deposit CuPc on an ITO film at a deposition rate of 0.2 to 0.4 nm/sec, whereby a CuPc layer having a thickness of 20 nm was formed. Then, a molybdenum boat with Sil-1 in it was heated up to 270° C. to vapor-deposit Sil-1 on the CuPc layer at a deposition rate of 0.4 to 0.6 nm/sec, whereby a Sil-1 layer having a thickness of 40 nm was formed.

When a voltage of 10 V was applied to the above-obtained organic EL device in the same manner as in

Example 12

Production of Organic EL Device

An organic EL device was obtained in the same manner as in Example 11 except that the Sil-1 was replaced with the silanamine derivative (Sil-3) obtained in Example 3.

When a voltage of 9 V was applied to the above-obtained organic EL device in the same manner as in Example 11, blue light emission at 150 cd/m$^2$ was observed. Table 14 shows the current density, brightness, luminous efficiency and light color in this case.

Example 13

Production of Organic EL Device

An organic EL device was obtained in the same manner as in Example 11 except that the Sil-1 was replaced with the silanamine derivative (Sil-4) obtained in Example 4.

When a voltage off 9.5 V was applied to the above-obtained organic EL device in the same manner as in Example 11, blue light emission at 1,000 cd/m$^2$ was observed. Table 14 shows the current density, brightness, luminous efficiency and light color in this case.

Example 14

Production of Organic EL Device

A organic EL device was obtained in the same manner as in Example 10 except that α-sexithiophene (to be abbreviated as T$_6$ hereinafter) as one of organic semiconductive oligomers and Sil-1 were used as hole-conducting layer materials.

In addition, the hole-conducting layer was formed in the following manner so as to have a two-layer structure. A molybdenum boat with TG in it was heated to vapor-deposit T$_6$ on an ITO film at a deposition rate of 0.1 to 0.3 nm/sec, whereby a T$_6$ layer having a thickness of 20 nm was formed. Then, a molybdenum boat with Sil-1 in it was heated up to 270° C. to vapor-deposit Sil-1 on the T$_6$ layer at a deposition rate of 0.4 to 0.6 nm/sec, whereby a Sil-1 layer having a thickness of 40 nm was formed.

When a voltage of 8 V was applied to the above-obtained organic EL device in the same manner as in Example 10, blue light emission at 250 cd/m$^2$ was observed. Table 14 shows the current density, brightness, luminous efficiency and light color in this case.

Example 15

Production of Organic EL Device

An organic EL device was obtained in the same manner as in Example 14 except that T$_6$ was replaced with 4,4'-bis-dithiophenyl-1,1'-biphenyl (to be abbreviated as BTBIBT hereinafter) which was one of organic semiconductive oligomers.

When a voltage of 9 V was applied to the above-obtained organic EL device in the same manner as in Example 14, blue light emission at 700 cd, /m$^2$ was observed. Table 14 shows the current density, brightness, luminous efficiency and light color in this case.

Example 16

Production of Organic EL Device

An organic EL device was obtained in the same manner as in Example 11 except that the Sil-1 was replaced with the silanamine derivative (Sil-7) obtained in Example 7.

When a voltage of 10 V was applied to the above-obtained organic EL device in the same manner as in Example 11, blue light emission at 100 cd/m$^2$ was observed. Table 14 shows the current density, brightness, luminous efficiency and light color in this case.

Example 17

Production of Organic EL Device

An organic EL device was obtained in the same manner as in Example 11 except that the Sil-1 was replaced with the silanamine derivative (Sil-8) obtained in Example 8.

When a voltage of 11 V was applied to the above-obtained organic EL device in the same manner as in Example 11, blue light emission at 120 cd/m$^2$ was observed. Table 14 shows the current density, brightness, luminous efficiency and light color in this case.

Example 18

Production of Organic EL Device

An organic EL device was obtained in the same manner as in Example 11 except that the Sil-1 was replaced with the silanamine derivative (Sil-9) obtained in Example 9.

When a voltage of 12 V was applied to the above-obtained organic EL device in the same manner as in ]Example 11, blue light emission at ]40 cd/m$^2$ was observed. Table 14 shows the current density, brightness, luminous efficiency and light color in this case.

Comparative Example 2

Production of Organic EL Device

An organic EL device was obtained in the same manner as in Example 10 except that hexaphenylcyclodisilazane was used as a hole-conducting layer material.

When a voltage of 13 V was applied to the above-obtained organic EL device in the same manner as in Example 10, blue light emission at 100 cd, /m$^2$ was observed. Table 14 shows the current density, brightness, luminous efficiency and light color in this case.

TABLE 14

| | Hole-conducting layer | | Applied voltage (V) | Current density (mA/cm$^2$) | Brightness (cd/m$^2$) | Luminous efficiency (lm/W) | Emitted light color |
|---|---|---|---|---|---|---|---|
| | Anode side | Cathode side | | | | | |
| Ex.10 | Sil-1*1 | | 9.5 | 3.2 | 114 | 1.2 | blue |
| Ex.11 | CuPc*2 | Sil-1*1 | 10 | 13 | 440 | 1.1 | blue |
| Ex.12 | CuPc*2 | Sil-3*3 | 9 | 5 | 150 | 1.0 | blue |
| Ex.13 | CuPc*2 | Sil-4*4 | 9.5 | 30 | 1,000 | 1.1 | blue |
| Ex.14 | T$_6$*5 | Sil-1*1 | 8 | 10 | 250 | 0.98 | blue |
| Ex.15 | BTBIBT*6 | Sil-1*1 | 9 | 25 | 700 | 0.98 | blue |
| Ex.16 | CuPc*2 | Sil-7*8 | 10 | 4.2 | 100 | 0.75 | blue |

TABLE 14-continued

| | Hole-conducting layer | | Applied voltage (V) | Current density (mA/cm$^2$) | Brightness (cd/m$^2$) | Luminous efficiency (lm/W) | Emitted light color |
|---|---|---|---|---|---|---|---|
| | Anode side | Cathode side | | | | | |
| Ex.17 | CuPc*2 | Sil-8*9 | 11 | 6.0 | 140 | 0.66 | blue |
| Ex.18 | CuPc*2 | Sil-9*10 | 12 | 4.4 | 140 | 0.83 | blue |
| CEx.2 | | Cyclodisilazane*7 | 13 | 4 | 100 | 0.60 | blue |

Ex. = Example, CEx. = Comparative Example
*1: Silanamine derivative obtained in Example 1
*2: Copper phthalocyanine
*3: Silanamine derivative obtained in Example 3
*4: Silanamine derivative obtained in Example 4
*5: α-sexithiophene
*6: 4,4'-bis-dithiophenyl-1,1'-biphenyl
*7: Hexaphenylcyclodisilazane
*8: Silanamine derivative obtained in Example 7
*9: Silanamine derivative obtained in Example 8
*10: Silanamine derivative obtained in Example 9

As is clearly shown in Table 14, the organic EL devices obtained in Examples 10 to 18 exhibit practically sufficient performance at a low actuation voltage of 8 to 12 V, and their luminous efficiency is as high as 0.66 to 1.2 1 m/W.

In contrast, the organic EL device obtained in Comparative Example 2 gives a brightness of only 100 cd/m$^2$ at a relatively high actuation voltage of 13 V. That is because voltage is consumed for hole injection since the ionization potential of hexaphenylcyclodisilazane is as high as 5.7 eV.

Evaluation on Capability of Thin Film Maintenance

A plate prepared by forming a 100 nm thick ITO film on glass substrate (supplied by HOYA Corp. under the name of NA 40) was subjected to ultrasonic washing, drying and UV ozone washing in the same manner as in Example 10, and then a Sil-1 layer having a thickness of 60 nm was formed on the ITO film in the same manner as in Example 10.

The above-obtained sample was exposed to air for 1 month, and observed through an optical microscope to see whether or not the Sil-1 layer was destroyed due to recrystallization.

As a result, no destruction of the Sil-1 layer due to recrystallization was found through the optical microscope. This result shows that Sil-1 has excellent ability to keep thin film properties.

On the other hand, when TPD was tested in the same manner as above, it was observed through an optical microscope that TPD underwent recrystallization. This result shows that TPD is inferior to Sil-1 in ability to keep thin film properties.

As detailed above, according to the present invention, there can be provided novel silanamine derivatives whose purification is easy, whose thin film shows slow recrystallization with time and whose ionization potential is low. Further, there can be provided an organic EL device that can be actuated at a low voltage.

What is claimed is:

1. An organic electroluminescence device which comprises (a) one or more layers comprising an organic light-emitting layer and (b) a pair of electrodes sandwiching said one or more layers, at least one of said layers containing a silanamine compound of the formula (I),

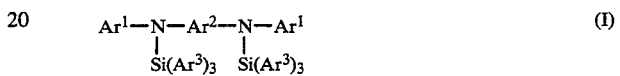

wherein:
each Ar$^1$ is independently an aryl group having 6 to 20 ring-forming carbon atoms which is unsubstituted or substituted with a substituent selected from the group consisting of an alkyl group having 1 to 6 carbon atoms, an alkoxy group having 1 to 6 carbon atoms, a phenoxy group, an alkyl-substituted phenoxy group and a vinyl group, Ar$^2$ is an arylene group having 6 to 20 ring forming carbon atoms which is unsubstituted or substituted with an alkyl group having 1 to 6 carbon atoms, and each Ar$^3$ is independently an aryl group having 6 to 12 ring forming carbon atoms which is unsubstituted or substituted with an alkyl group having 1 to 3 carbon atoms.

2. The organic electroluminescence device according to claim 1, wherein the layer containing the silanamine compound is a hole-conducting layer or the organic light-emitting layer.

3. The organic electroluminescence device according to claim 1, which has a structure selected from the group consisting of (1) anode/organic light-emitting layer/cathode, (2) anode/hole-conducting layer/organic light-emitting layer/cathode, (3) anode/organic light-emitting layer/electron-injecting layer/cathode and (4) anode/hole-conducting layer/organic light-emitting layer/electron-injecting layer/cathode.

4. The organic electroluminescence device according to claim 1, which consists essentially of anode/organic light-emitting layer containing the silanamine compound/cathode.

5. The organic electroluminescence device according to claim 1, which consists essentially of anode/hole-conducting layer containing the silanamine compound/organic light-emitting layer/cathode.

6. The organic electroluminescence device according to claim 1, which consists essentially of anode/hole-conducting layer containing tile silanamine compound/organic light-emitting layer/electron-injecting layer/cathode.

7. The organic electroluminescence device according to claim 1, wherein said aryl group of Ar$^1$ is selected from the group consisting of phenyl, biphenyl, naphthyl, anthranyl, phenanthryl and pyrenyl.

8. The organic electroluminescence device according to claim 7, wherein said aryl group of $Ar^1$ is substituted by a substituent selected from the group consisting of methyl, ethyl, n-propyl, i-propyl, n-butyl, i-butyl, s-butyl, t-butyl, n-pentyl and n-hexyl.

9. The organic electroluminescence device according to claim 7, wherein said aryl group of $Ar^1$ is substituted by a substituent selected from the group consisting of methoxy, ethoxy, propoxy, butoxy, pentoxy and hexoxy.

10. The organic electroluminescence device according to claim 7, wherein said aryl group of $Ar^1$ is substituted by a phenoxy group substituted with an alkyl group having 1 to 6 carbon atoms.

11. The organic electroluminescence device according to claim 7, wherein said arylene group of $Ar^2$ is selected from the group consisting of phenylene, biphenylene, naphthylene, anthranylene, phenanthrylene and pyrenylene.

12. The organic electroluminescence device according to claim 7, wherein said arylene group of $Ar^2$ is substituted with a substituent selected from the group consisting of methyl, ethyl, n-propyl, i-propyl, n-butyl, i-butyl, s-butyl, t-butyl, n-pentyl and n-hexyl.

13. The organic electroluminescence device according to claim 12, wherein said aryl group of $Ar^3$ is selected from the group consisting of phenyl, biphenyl, naphthyl, anthranyl, phenanthryl and pyrenyl.

14. The organic electroluminescence device according to claim 12 wherein said aryl group of $Ar^3$ is substituted by a substituent selected from the group consisting of methyl, ethyl, n-propyl and i-propyl.

15. The organic electroluminescence device according to claim 1, wherein the silanamine compound has an ionization potential of 5.6 eV or less.

16. The organic electroluminescence device according to claim 1, wherein the silanamine compound is selected from the group consisting of

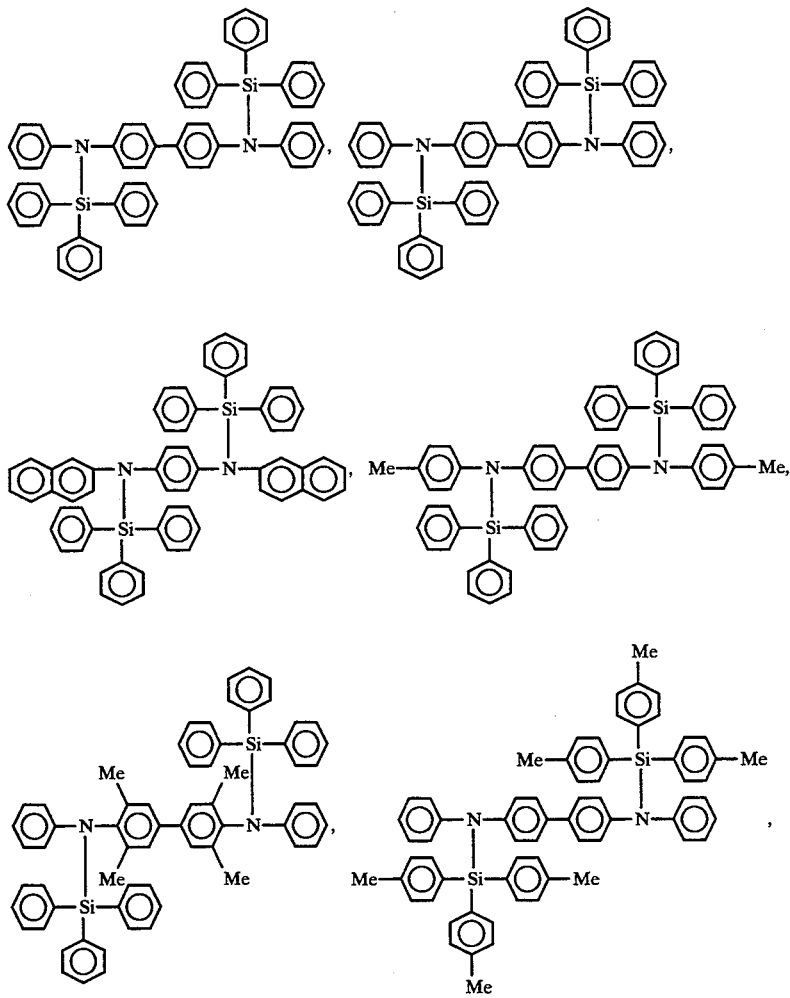

-continued
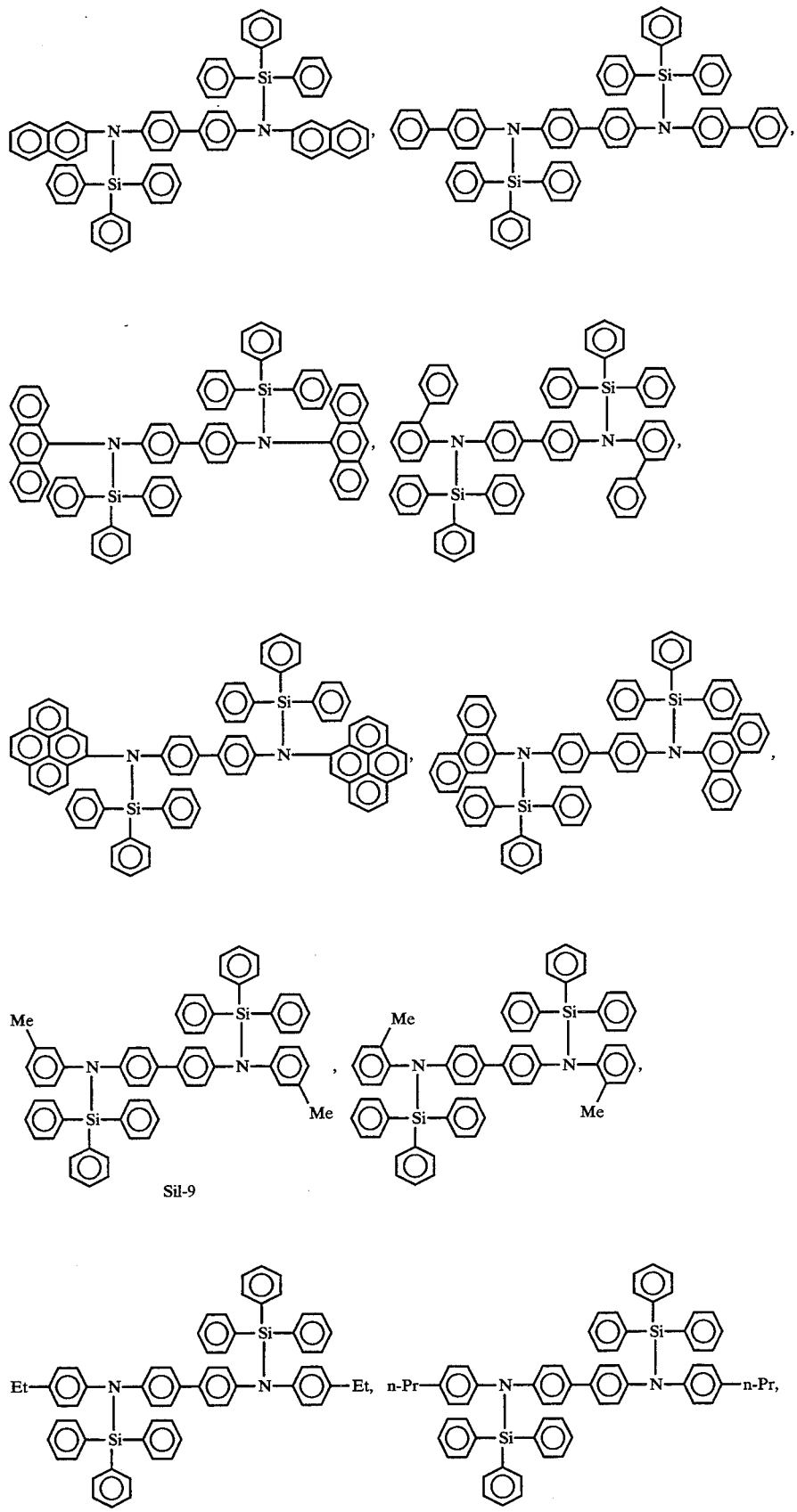

-continued
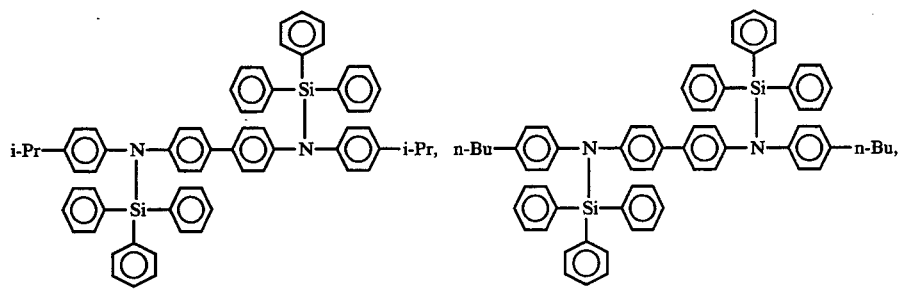
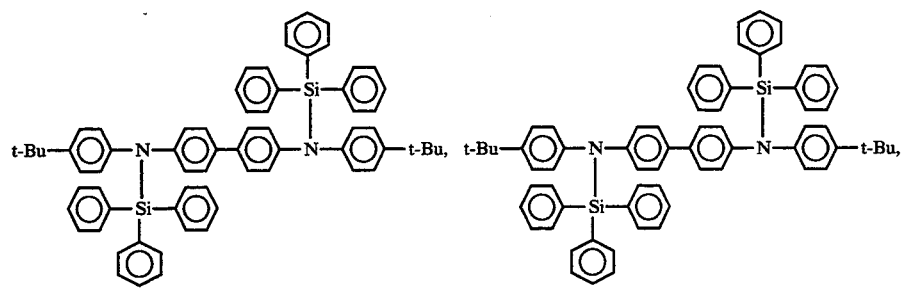
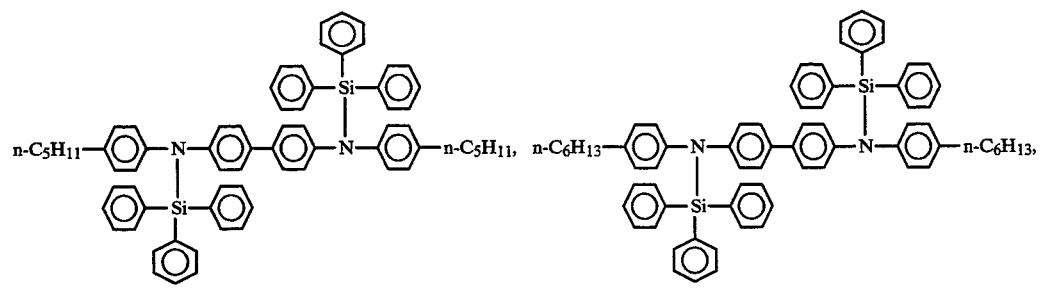
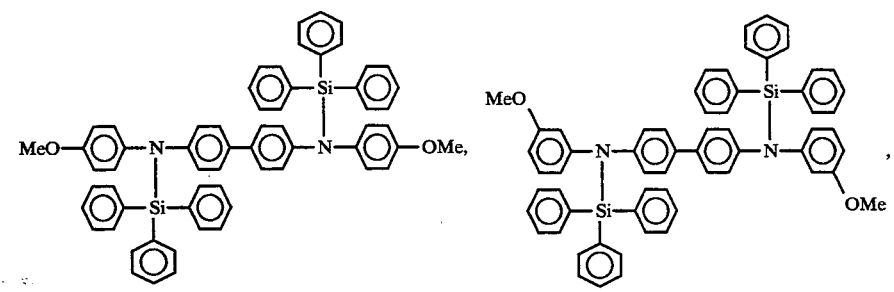
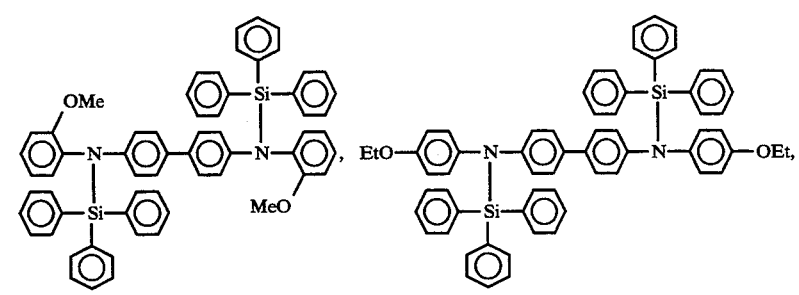

-continued
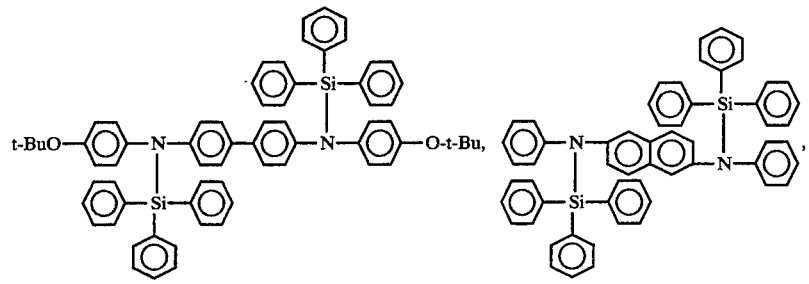
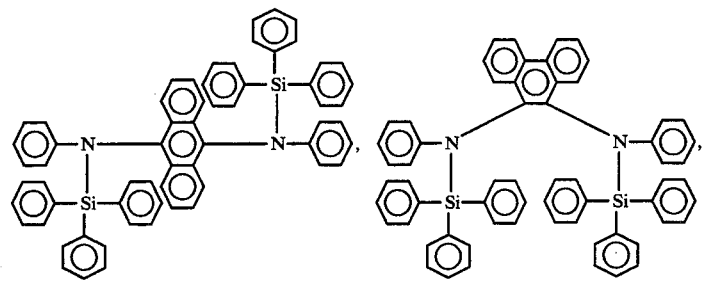
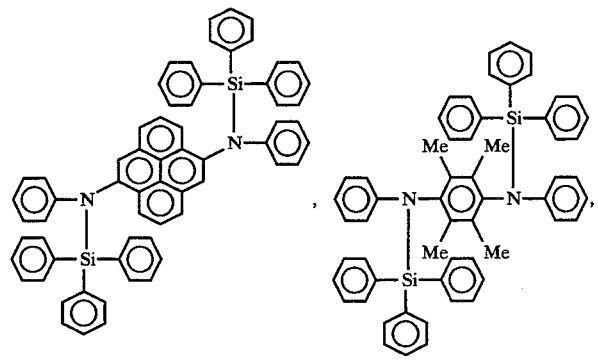
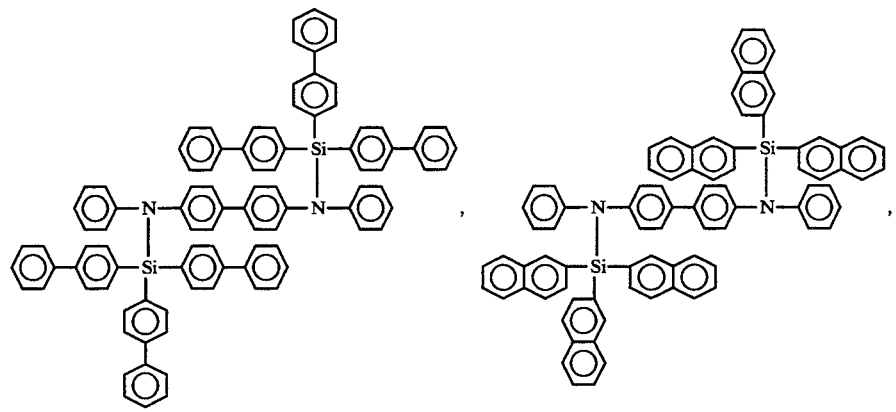

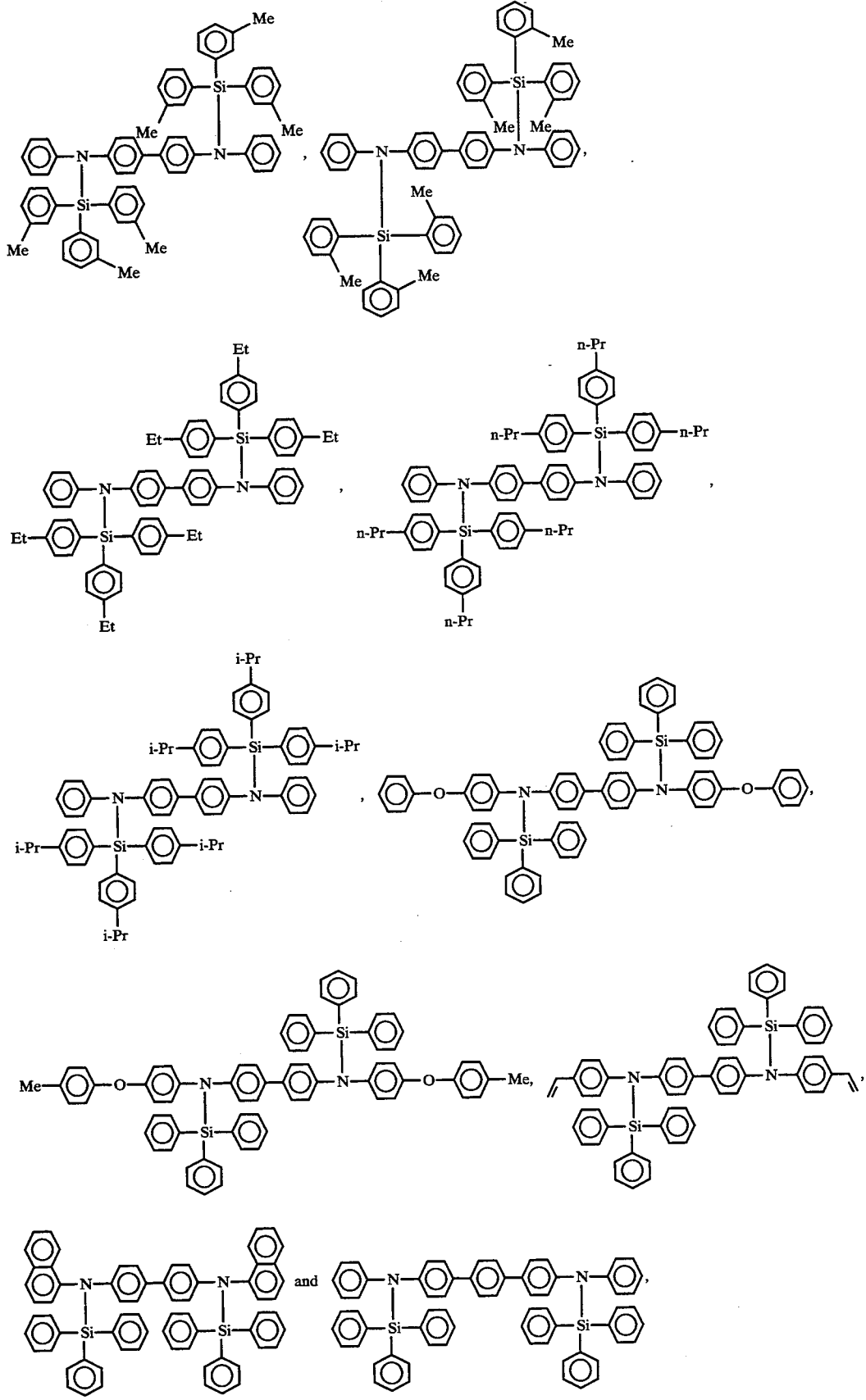
wherein Me is methyl, Et is ethyl, n-Pr is n-propyl, i-Pr is i-propyl, n-Bu is n—butyl and t—Bu is t-butyl.
* * * * *